UnitedStates Patent (12)
Straka

(10) Patent No.: US 7,815,921 B2
(45) Date of Patent: Oct. 19, 2010

(54) CYTOCAPACITY TEST FOR THE PREDICTION OF THE HEMATOPOIETIC RECOVERY, NEUTROPENIC FEVER, AND ANTIMICROBIAL TREATMENT FOLLOWING HIGH-DOSE CYTOTOXIC CHEMOTHERAPY

(75) Inventor: Christian Straka, Pöcking (DE)

(73) Assignee: Ludwid Maximilians Universitat, Munich (DE)

( * ) Notice: Subject to any disclaimer, the term of this patent is extended or adjusted under 35 U.S.C. 154(b) by 650 days.

(21) Appl. No.: 10/508,509

(22) PCT Filed: Mar. 24, 2003

(86) PCT No.: PCT/EP03/03056

§ 371 (c)(1),
(2), (4) Date: Sep. 21, 2004

(87) PCT Pub. No.: WO03/081238

PCT Pub. Date: Oct. 2, 2003

(65) Prior Publication Data

US 2005/0158703 A1    Jul. 21, 2005

(30) Foreign Application Priority Data

Mar. 22, 2002    (EP) .................................. 02006609

(51) Int. Cl.
*A61K 45/00* (2006.01)
*A61K 35/28* (2006.01)
(52) U.S. Cl. ..................................... 424/278.1; 424/577
(58) Field of Classification Search .................. None
See application file for complete search history.

(56) References Cited

OTHER PUBLICATIONS

Breems D. A. et al., "Individual Stem Cell Quality in Leukapheresis Product is Related to the Number of Mobilized Stem Cells," *Blood* vol. 87, No. 12, pp. 5370-5378 (1996).
Copelan E. A. et al., "Analysis of Factors Predicting Speed of Hematopoietic Recovery Using Progenitor Cells Mobilized with Etoposide and G-CSF," *Blood* vol. 94, No. 10, Suppl. 1, Part 1, p. 140a (1999).
Hassan H. T. et al., "Thrombocytopenia After High-Dose Chemotherapy and Autologous Stem Cell Transplantation: An Unresolved Problem and Possible Approaches to Resolve It," *Medline US National Library of Medicine (NLM)* vol. 5, No. 4, pp. 407-414 (1996).
Porrata et al., "Early Lymphocyte Recovery Predicts Superior Survival After Autologous Hematopoietic Stem Cell Transplantation in Multiple Myeloma or Non-Hodgkin's Lymphoma, " *Blood* vol. 96, No. 11, Part 1, p. 559a (2000).
Porrata et al., "Early Lymphocyte Recovery Predicts Superior Survival After Autologous Hematopoietic Stem Cell Transplantation in Multiple Myeloma or Non-Hodgkin's Lymphoma, " *Blood* vol. 98, No. 3, pp. 579-585 (2001).

Sola C. et al., "Prognostic Factors of Peripheral Blood Stem Cell Mobilization with Cyclophosphamide and Filgrastim (r-metHuG-CSF): The CD34cell Dose Positively Affects the Time to Hematopoietic Recovery and Supportive Requirements After High-Dose Chemotherapy," *Elsevier Science Publishers* vol. 4, No. 3 pp. 195-209 (2002).
Arseniev et at., "Transient Increase of Leukocytes After Transplantation of Expanded and Nonexpanded Allogeneic CD34+ Blood Cells is of Host Origin," *Blood*; 89:1116-1118 (1997).
Asano, "Human Granulocyte Colony-Stimulating Factor: Its Basic Aspects and Clinical Applications," *The American Journal of Pediatric Hematology/Oncology*; 13:400-413 (1991).
Attal et al., "A Prospective, Randomized Trial of Autologous Bone Marrow Transplantation and Chemotherapy in Multiple Myeloma," *N. Engl J Med*; 335:91-97 (1996).
Barlogie et al., "Superiority of Tandem Autologous Transplantation Over Standard Therapy for Previously Untreated Multiple Myeloma," *Blood*; 89:789-793 (1997).
Bensinger et al., "Factors That Influence Collection and Engraftment of Autologous Peripheral-Blood Stem Cells," *J Clin Oncol*; 13:2547-2555 (1995).
Beyer et al., "Hematopoietic Rescue After High-Dose Chemotherapy Using Autologous Peripheral-Blood Progenitor Cells of Bone Marrow: A Randomized Comparison," *J Clin Oncol*; 13:1328-1335 (1995).
Blay et al., "Early Lymphopenia After Cytotoxic Chemotherapy as a Risk Factor for Febrile Neutropenia," *J Clin Oncol*; 14:636-643 (1996).
Bodey et al., "Quantitative Relationships Between Circulating Leukocytes and Infection in Patients with Acute Leukemia," *Ann Intern Med*; 64:328-340 (1966).
Bolwell et al., "Platelet transfusion requirements during autologous peripheral blood progenitor cell transplantation correlate with the pretransplant platelet count," *Bone Marrow Transplant*; 20:459-463 (1997).

(Continued)

*Primary Examiner*—Michail A Belyavskyi
(74) *Attorney, Agent, or Firm*—Finnegan, Henderson, Farabow, Garrett & Dunner, LLP

(57) ABSTRACT

The present invention relates to a method for determining the hematopoietic cytocapacity of a subject comprising the steps of: (a) determining the amount of leukocytes present in a blood sample obtained from a subject, wherein said subject has been subjected to administration of a single dose of G-CSF and has been maintained for a time sufficient to allow mobilization or release of the leukocytes from hematopoietic production and storage tissues and sites of margination into the blood; and (b) determining the hematopoietic cytocapacity by assessing the amount of leukocytes determined in step (a) with the amount of leukocytes which have been mobilized or released in a control subject wherein said control subject is selected from the group consisting of subjects having (i) a high risk for a disease, disorder or complication associated with high-dose cytotoxic chemotherapy and/or hematopoietic cell transplantation, (ii) an intermediate risk for a disease, disorder or complication associated with high-dose cytotoxic chemotherapy and/or hematopoietic cell transplantation or (iii) a low risk for a disease, disorder or complication associated with high-dose cytotoxic chemotherapy and/or hematopoietic cell transplantation.

24 Claims, 5 Drawing Sheets

OTHER PUBLICATIONS

Figure 1:
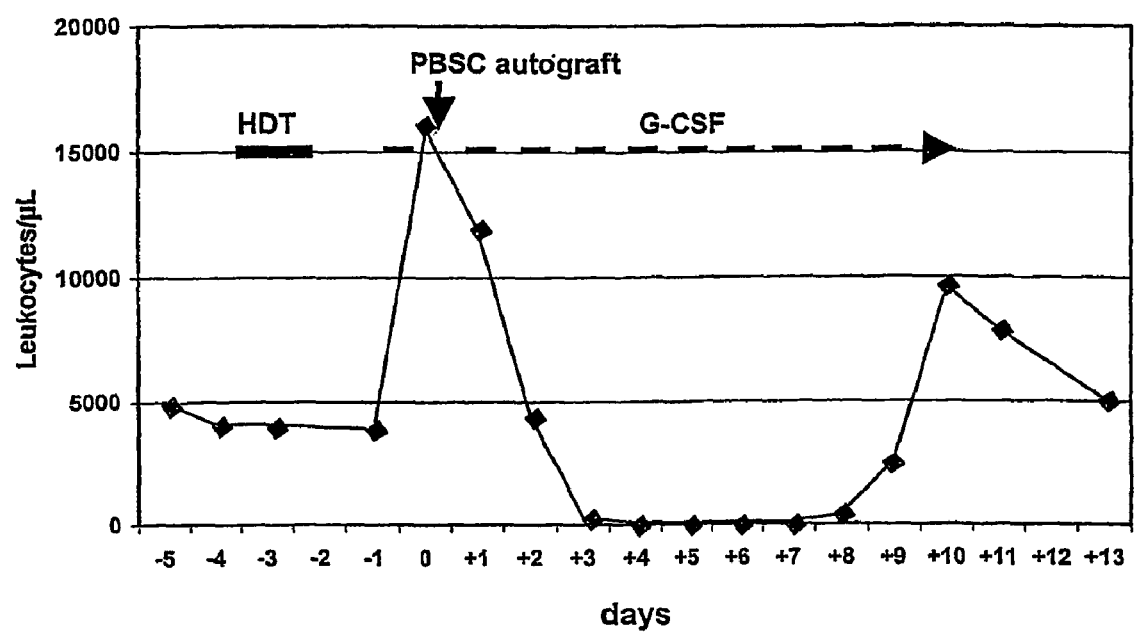

Bronchud et al., In Vitro and in vivo analysis of the effects of recombinant human granulocyte colony-stimulating factor in patients, *Br J Cancer*, 58:64-69 (1988).

Chatta et al., "Effects of In Vivo Recombinant Methionyl Human Granulocyte Colony-Stimulating Factor on the Neutrophil Response and Peripheral Blood Colony-Forming Cells in Healthy Young and Elderly Adult Volunteers," *Blood*; 84:2923-2929 (1994).

Cox, "Regression Models and Life-Tables," *J. Roy Stat Soc*; (B) 34:187-202 (1972).

Dührsen et al., "Effects of Recombinant Human Granulocyte Colony-Stimulating Factor on Hematopoietic Progenitor Cells in Cancer Patients," *Blood*; 72:2074-2081 (1988).

Freifeld et al., "A Double-Blind Comparison of Empirical Oral and Intravenous Antibiotic Therapy for Low-Risk Febrile Patients with Neutropenia During Cancer Chemotherapy," *N Engl J Med*; 341: 305-311 (1999).

Fujita et al., "Augmentation of megakaryocytopoiesis within the hematopoietic microenvironment of human granulocyte colony-stimulating factor transgenic mice," *Exp Hematol*; 29:1010-1018 (2001).

Gabrilove et al., "Phase I Study of Granulocyte Colony-stimulating Factor in Patients with Transitional Cell Carcinoma of the Urothelium," *J Clin Invest*; 82: 1454-1461 (1988).

Herrmann et al., "Infections in patients managed at home during autologous stem cell transplantation for lymphoma and multiple myeloma," *Bone Marrow Transplant*, 24:1213-1217 (1999).

Hughes et al., "1997 Guidelines for the Use of Antimicrobial Agents in Neutropenic Patients with Unexplained Fever," *Clin Infect Dis*; 25:551-573 (1997).

Kaplan et al., "Nonparametric Estimation From Incomplete Observations," *J Am Stat Ass*; 53:457-481 (1958).

Kawakami et al., "Levels of Serum Granulocyte Colony-Stimulating Factor in Patients With Infections," *Blood*; 76:1962-1964 (1990).

Kern et al.,"Oral Verus Intravenous Empirical Antimicrobial Therapy for Fever in Patients With Granulocytopenia Who Are Receiving Cancer Chemotherapy," *N Engl J Med*; 341:312-318 (1999).

Ketterer et al., "High $CD34^+$ Cell Counts Decrease Hematologic Toxicity of Autologous Peripheral Blood Progenitor Cell Transplantation," *Blood*; 91:3148-3155 (1998).

Klastersky et al., "The Multinational Association for Supportive Care in Cancer Risk Index: A Multinational Scoring System for Identifying Low-Risk Febrile Neutropenic Cancer Patients," *J Clin Oncol*; 18:3038-3051 (2000).

Kolbe et al., "Infectious complications during neutropenia subsequent to peripheral blood stem cell transplantation," *Bone Marrow Transplant*; 19:143-147 (1997).

Kubota et al., "Structural Characterization of Natural and Recombinant Human Granulocyte Colony-Stimulating Factors," *J. Biochem.*; 107:486-492 (1990).

Laterveer et al., "Interleukin-8 Induces Rapid Mobilization of Hematopoietic Stem Cells With Radioprotective Capacity and Long-Term Myelolymphoid Repopulating Ability," *Blood*; 85(8):2269-75, (1995).

Laterveer et al., "Rapid Mobilization of Hematopoietic Progenitor Cells in Rhesus Monkeys by a Single Intravenous Injection of Interleukin-8," *Blood*; 87(2):781-88, (1996).

Lenhoff et al., "Impact on survival of high-dose therapy with autologous stem cell support in patients younger than 60 years with newly diagnosed multiple myeoloma: a population-based study," *Blood*; 95:7-11 (2000).

Lieschke et al., "Mice Lacking Granulocyte Colony-Stimulating Factor have Chronic Neutropenia, Granulocyte and Macrophage Progenitor Cell Deficiency, and Impaired Neutrophil Mobilization," *Blood*; 84:1737-1746 (1994).

Linch et al., "Dose intensification with autologous bone-marrow transplantation in relapsed and resistant Hodgkin's disease: results of a BNLI randomised trial," *Lancet*; 341:1051-1054 (1993).

Link et al., "Interventional antimicrobial therapy in febrile neutropenic patients," *Ann. Hematol.*; 69:231-243 (1994).

Lord et al, "The kinetics of human granulopoiesis following treatment with granulocyte colony-stimulating factor in vivo," *Proc. Natl. Acad. Sci. USA*; 86:9499-9503 (1989).

Meisenberg et al., "Outpatient High-Dose Chemotherapy With Autologous Stem-Cell Rescue for Hematologic and Nonhematologic Malignancies," *J Clin Oncol*; 15:11-17 (1997).

Molineux et al., "Transplantation Potential of Peripheral Blood Stem Cells Induced by Granulocyte Colony-Stimulating Factor," *Blood*; 76:2153-2158 (1990).

Morstyn et al., "Effect of Granulocyte Colony Stimulating Factor on Neutropenia Induced by Cytotoxic Chemotherapy," *Lancet*; 1:667-672 (1988).

Morstyn et al., "Treatment of Chemotherapy-Induced Neutropenia by Subcutaneously Administered Granulocyte Colony-Stimulating Factor With Optimization of Dose and Duration of Therapy," *J Clin Oncol*; 7:1554-1562 (1989).

Noursadeghi et al., "Production of Granulocyte Colony-Stimulating Factor in the Nonspecific Acute Phase Response Enhances Host Resistance to Bacterial Infection," *J Immunol*; 169:913-919 (2002).

Ozer et al., "2000 Update of Recommendations for the Use of Hematopoietic Colony-Stimulating Factors: Evidence-Based, Clinical Practice Guidelines," J Clin Oncol; 18:3558-3585 (2000).

Palumbo et al.,"Dose-Intensive Melphalan With Stem Cell Support (MEL100) Is Superior to Standard Treatment in Elderly Myeloma Patients," *Blood*; 94:1248-1253 (1999).

Peto et al., "Asymptotically Efficient Rank Invariant Test Procedures," *J R Stat Soc A*; 135:185-206 (1972).

Pettengell et al., "Peripheral Blood Progenitor Cell Transplantation in Lymphoma and Leukemia Using a Single Apheresis," *Blood*; 82:3770-3777 (1993).

Philip et al., "Autologous Bone Marrow Transplantation As Compared with Salvage Chemotherapy in Relapses of Chemotherapy-Sensitive Non-Hodgkin's Lymphoma," *N Engl J Med*; 333:1540-1545 (1995).

*N. Engl. J. Med* 1996; 334:990.

Pizzo, "Management of Fever in Patients with Cancer and Treatment-Induced Neutropenia," *N Engl J Med*; 328: 1323-1332 (1993).

Reich et al., "Infectious complications after high-dose chemotherapy and autologous stem cell transplantation: comparison between patients with lymphoma or multiple myeloma and patients with solid tumors," *Bone Marrow Transplant*; 27: 525-529 (2001).

Rubenstein et al., "Outpatient Treatment of Febrile Episodes in Low-Risk Neutropenic Patients with Cancer," *Cancer*, 71:3640-3646 (1993).

Schiller et al., "Phase I-II study of busulfan and cyclophosphamide conditioning for transplantation in advanced multiple myeloma," *Bone Marrow Transplant*; 14:131-136 (1994).

Schmitz et al., "Randomised trial of filgrastim-mobilised peripheral blood progenitor cell transplantation versus autologous bone-marrow transplantation in lymphoma patients," *Lancet*; 347:353-357 (1996).

Silber et al., "First-Cycle Blood Counts and Subsequent Neutropenia, Dose Reduction, or Delay in Early-Stage Breast Cancer Therapy," *J Clin Oncol*; 16:2392-2400 (1998).

Sutherland et al., "The ISHAGE Guidelines for CD34+ Cell Determination by Flow Cytometry," *J Hematotherapy*, 5:213-226 (1996).

Talcott et al.,"Risk Assessment in Cancer Patients With Fever and Neutropenia: A Prospective, Two-Center Validation of a Prediction Rule," *J Clin Oncol*; 10:316-322 (1992).

Talcott et al., "Home Antibiotic Therapy for Low-Risk Cancer Patients With Fever and Neutropenia: A Pilot Study of 30 Patients Based on a Validated Prediction Rule," *J Clin Oncol*; 12:107-114 (1994).

Terashima et al., "Release of Polymorphonuclear Leukocytes From the Bone Marrow by Interleukin-8," *Blood*; 92(3):1062-69, (1998).

Tricot et al., "Peripheral Blood Stem Cell Transplants for Multiple Myeolma: Identification of Favorable Variables for Rapid Engraftment in 225 Patents," *Blood*; 85:588-596 (1995).

Watari et al., "Serum Granulocyte Colony-Stimulating Factor Levels in Healthy Volunteers and Patients With Various Disorders as Estimated by Enzyme Immunoassay," *Blood*; 73:117-122 (1989).

Weaver et al., "High-dose chemotherapy with BUCY or BEAC and unpurged peripheral blood stem cell infusion in patients with low-grade non-Hodgkin's lymphoma," *Bone Marrow Transplant*; 21:383-389 (1998).

Weaver et al., "An Analysis of Engraftment Kinetics as a Function of the CD34 Content of Peripheral Blood Progenitor Cell Collections in 692 Patients After the Administration of Myeloablative Chemotherapy," *Blood*; 86:3961-3969 (1995).

Welte et al., "Filgrastim (r-metHuG-CSF): The First 10 Years," *Blood*; 88:1907-1929 (1996).

Straka et al., "Responsiveness to G-CSF before leukopenia predicts defense to infection in high-dose chemotherapy recipients," *Blood*; 104:1989-1994 (2004).

Notice of Grounds for Rejection issued in Japanese Patent Application No. 2003-578921 on Oct. 30, 2008.

Tatsumi et al., "Timing of Collection and Method of Collection of Peripheral Blood Stem Cells," Igakuno-Ayumi, 176(9):574-578 (1996).

CYTOCAPACITY TEST FOR THE PREDICTION OF THE HEMATOPOIETIC RECOVERY, NEUTROPENIC FEVER, AND ANTIMICROBIAL TREATMENT FOLLOWING HIGH-DOSE CYTOTOXIC CHEMOTHERAPY

The present invention relates to a method for determining the hematopoietic cytocapacity of a subject comprising the steps of: (a) determining the amount of leukocytes present in a blood sample obtained from a subject, wherein said subject has been subjected to administration of a single dose of G-CSF and has been maintained for a time sufficient to allow mobilization or release of the leukocytes from hematopoietic production and storage tissues and sites of margination into the blood; and (b) determining the hematopoietic cytocapacity by assessing the amount of leukocytes determined in step (a) with the amount of leukocytes which have been mobilized or released in a control subject wherein said control subject is selected from the group consisting of subjects having (i) a high risk for a disease, disorder or complication associated with high-dose cytotoxic chemotherapy and/or, hematopoietic cell transplantation, (ii) an intermediate risk for a disease, disorder or complication associated with high-dose cytotoxic chemotherapy and/or hematopoietic cell transplantation or (iii) a low risk for a disease, disorder or complication associated with high-dose cytotoxic chemotherapy and/or hematopoietic cell transplantation. The present invention also relates to a method for selecting a suitable antimicrobial prophylaxis or therapy, a suitable prophylaxis or therapy for neutropenic fever, a suitable amount of CD34$^+$ cells for transplantation, a suitable amount of a hematopoietic growth factor for a subject or a suitable level of supportive care. Finally, encompassed by the present invention is the use of leukocytes obtained from a subject for the preparation of a diagnostic composition for diagnosing a susceptibility for a disease, disorder or complication associated with high-dose cytotoxic therapy and/or hematopoietic cell transplantation in said subject, wherein said subject has been subjected to administration of a single dose of G-CSF and has been maintained for a time sufficient to allow mobilization or release of the leukocytes from hematopoietic production and storage tissues and sites of margination into the blood.

The myelosuppression and hematopoietic recovery after cytotoxic chemotherapy for malignancies is the major determinator of the treatment-related morbidity and mortality (Bodey 1966; Link 1994). The transplantation of autologous hematopoietic stem and progenitor cells harvested from bone marrow or the peripheral blood can rescue the host hematopoietic functions after high-dose therapy. High-dose therapy showed favorable disease control and survival in patients with lymphoma or multiple myeloma (Philip 1995; Attal 1996; Barlogie 1997; Lenhoff 2000). The use of mobilized peripheral blood stem cells (PBSCs) has almost completely replaced the use of autologous bone marrow as a graft because of a faster engraftment (Beyer 1995; Schmitz 1996). The CD34$^+$ cell number in the PBSC graft is a marker for the stem and progenitor cell quantity and related with the hematopoietic recovery. Although the number of CD34$^+$ cells can be precisely determined, a large variability in the prediction of the hematopoietic recovery remains (Bensinger 1995; Tricot 1995; Weaver 1995; Ketterer 1998). Host factors which play a role in the hematopoietic recovery after cytotoxic therapy are poorly defined (Tricot 1995; Bolwell 1997).

Neutropenia after high-dose therapy usually is short with the use of mobilized PBSCs, yet it is severe for some days. The majority of patients develop neutropenic fever indicating infection (Kolbe 1997; Reich 2001). The clinical course of infection is variable and in a proportion of the patients complications can become life-threatening.

Granulocyte colony-stimulating factor (G-CSF) is a hematopoietic growth factor specific for neutrophil production and function. It increases the proliferation rate of neutrophil progenitor cells in the bone marrow and accelerates the neutrophil maturation (Lord 1989). The major applications of G-CSF today are to reduce the risk of neutropenic fever and to mobilize PBSCs (Ozer 2000).

A risk assessment for a myelosuppressed subject, if possible, could be used to define different levels of supportive care, to stratify the application and dose of hematopoietic growth factors and intensity and duration of antimicrobial prophylaxis and therapy.

Thus, the technical problem underlying the present invention is to provide means and methods for the prediction, diagnosis, prognosis and treatment of diseases, disorders or complications associated with high-dose cytotoxic chemotherapy and/or hematopoietic cell transplantation whereby the aforementioned undesirable side effects are to be avoided, ameliorated or treated adequately.

The technical problem underlying the present invention is solved by the embodiments characterized in the claims.

Accordingly, the present invention relates to a method for determining the hematopoietic cytocapacity of a subject comprising the steps of:
  (a) determining the amount of leukocytes present in a blood sample obtained from a subject, wherein said subject has been subjected to administration of a single dose of G-CSF and has been maintained for a time sufficient to allow mobilization or release of the leukocytes from hematopoietic production and storage tissues or sites of margination into the blood; and
  (b) determining the hematopoietic cytocapacity by assessing the amount of leukocytes determined in step (a) with the amount of leukocytes which have been mobilized or released in a control subject wherein said control subject is selected from the group consisting of subjects having (i) a high risk for a disease, disorder or complication associated with high-dose cytotoxic chemotherapy and/or hematopoietic cell transplantation, (ii) an intermediate risk for a disease, disorder or complication associated with high-dose cytotoxic chemotherapy and/or hematopoietic cell transplantation or (iii) a low risk for a disease, disorder or complication associated with high-dose cytotoxic chemotherapy and/or hematopoietic cell transplantation or a susceptibility therefor.

In one preferred embodiment, the invention relates to the above method wherein in step (b), the control subject is a healthy subject. In a further preferred embodiment of the invention, the assessment is carried out by comparison of the leukocyte number determined in step (a) with a stored number or range of leukocyte numbers of a control subject or control subjects, which is (are) preferably (a) healthy subject(s).

Further, it is envisaged by the present invention that in step (b) the amount of leukocytes is present in a blood sample from the control subject in which said leukocytes have been mobilized or released.

The term "hematopoietic cytocapacity" refers to a value which is predictive for diagnosis, prognosis and treatment of diseases, disorders or complications associated with high-dose cytotoxic chemotherapy and/or hematopoietic cell transplantation. Said value can be determined as described below and in the accompanied Examples. It represents the leukocytes which are induced due to administration of a single dose of G-CSF in a subject after cytotoxic therapies, such as high-dose chemotherapy. The hematopoietic cytocapacity expresses the impact of the induced leukocyte peaks on a relative scale and/or categorization. The hematopoietic cytocapacity may be calculated by categorizing the distribution of the leukocyte peaks into <25. percentile, >25. percentile, <50. percentile, >50. percentile, <75. percentile and >75. percentile, or a transformation into relative values with respect to the median of the distribution which can be set as 1.0; see also accompanying examples.

The term "leukocytes" encompasses B and T lymphocytes, granulocytes, (eosinophiles, neutrophiles, basophiles), monocytes and macrophages as well as precursors thereof or cells which are derived therefrom.

The term "subject" as used in accordance with this invention relates to animals, preferably to vertebrates, and humans.

The term "administration" as used herein refers to all suitable modes of administration for a protein or polypeptide, such as G-CSF. Such modes of administration comprise intravenous and subcutaneous administration of G-CSF. Moreover, the substance can be administered in combination with other substances either in a common pharmaceutical composition or as separated pharmaceutical compositions.

The term "a single dose" means that G-CSF is administered a defined time interval prior to the determination of the hematopoietic cytocapacity to the patient and to further steps of medical treatment, such as transplantation of PBSCs or hematopoietic growth factor or antimicrobial treatment to the subject. However, said term does not necessarily require that G-CSF is only administered once, rather the single dose of G-CSF can also be administered in several steps independently. The single dose of G-CSF to be administered in accordance with the method of the invention may be given before, during, or after cytotoxic therapy. Preferably, the said single dose is administered after cytotoxic therapy has been given. Administration of the said single dose of G-CSF during cytotoxic therapy is preferably contemplated where the course of such cytotoxic therapy comprises several administrations of the therapeutic agent(s) for such cytotoxic therapy, so that the said single dose of G-CSF is administered when a first administration of a dose of a therapeutic agent for such cytotoxic therapy has been administered, but before the last dose of the same or another therapeutic agent for such cytotoxic therapy has been administered. More preferably, said time period is in the range of about 1 to about 120 hours. Still more preferably, said time period is about 1 hour, about 2 hours, about 6 hours, about 10 hours, about 12 hours, about 14 hours or about 18 hours.

In another embodiment of the invention, the single dose G-CSF may be administered independently of a cytotoxic therapy and/or of hematopoietic cell transplantation. The term "hematopoietic cytocapacity" may thus also refer to a value which is predictive for diagnosis, prognosis and treatment of diseases, disorders or complications associated with infection. Said value can be determined as described below and in the accompanied Examples, independently of prior treatment of the patient with cytotoxic therapy and/or hematopoietic cell transplantation. It represents the leukocytes which are induced due to administration of a single dose of G-CSF in a subject. The hematopoietic cytocapacity expresses the impact of the induced leukocyte peaks on a relative scale. The hematopoietic cytocapacity may be calculated by categorizing the distribution of the leukocyte peaks into <25. percentile, >25. percentile, <50. percentile, >50. percentile, <75. percentile and >75. percentile, or a transformation into relative values with respect to the median of the distribution which can be set as 1.0; see also accompanying examples. Further, the term "a single dose" may thus also mean that G-CSF is administered a defined time interval prior to the determination of the hematopoietic cytocapacity to the subject independently of further steps of medical treatment, such as hematopoietic growth factor or antimicrobial treatment or hematopoietic transplantation to the subject. Said term does not necessarily require that G-CSF is only administered once, rather the single dose of G-CSF can also be administered in several steps. The single dose of G-CSF to be administered in accordance with the method of the invention may be given independently of cytotoxic therapy, and/or without any cytotoxic therapy.

The term "G-CSF" refers to polypeptides or proteins having the biological activity of granulocyte-colony stimulating factor as described in Filgrastim (r-metHu G-CSF) in clinical practice, Eds. George Morstyn, Second Edition 1998, Marcel Dekker Inc., New York; Kubota 1990; Asano 1991; Welte 1996. The terms polypeptide and protein are used synonymously herein. Preferably, said G-CSF proteins or polypeptides have an amino acid sequence of at least the mature sequence of G-CSF as shown in Genbank accession number CAA27291 (SEQ ID No: 1) or CAA27290 (SEQ ID No: 2), wherein amino acids 1 to 30 correspond to the signal sequence and amino acids 31 to 207 correspond to the mature polypeptide responsible for the biological activity of G-CSF. Moreover, the amino acid sequence as shown in Genbank accession number CM01330 (SEQ ID No: 3) or CAA01319 (SEQ ID No: 4) also correspond to the mature G-CSF polypeptide. Therapeutically suitable G-CSF compositions are commercially available and are described in detail below. The G-CSF polypeptides or proteins, furthermore, encompass molecular variants having an amino acid sequence which is at least 70%, at least 80%, at least 85%, at least 90%, at least 92%, at least 95%, at least 96%, at least 97%, at least 98% or at least 99% identical to any one of the aforementioned sequences. In a preferred embodiment of the invention, a G-CSF variant having any of the sequences provided in EP0459630 may be used. Also, a modified sequence of G-CSF may be prepared in accordance with the teachings of EP0459630, and the G-CSF so prepared may be used in accordance with the present invention. Preferably, said molecular variants having the biological activities of G-CSF as described above. Moreover, fragments of G-CSF having the biological activities of G-CSF as described above, are also encompassed in accordance with the method of the present invention. Those fragments may comprise N- and C-terminal deletions of the mature G-CSF polypeptides. Finally, also within the scope of the method of the present invention are fusion proteins of the aforementioned G-CSF proteins, molecular variants or fragments thereof. Said fusion proteins comprise in addition to the said G-CSF proteins, molecular variants or fragments thereof further amino acid sequences which can be derived from proteins which are not related to G-CSF, such as antibodies. However, said fusion proteins have to exhibit the biological activities of G-CSF referred to herein. The present invention encompasses also all suitable chemical modifications of the aforementioned proteins and polypeptides like pegylation. The process of pegylation is known to the person of skill in the art. U.S. Pat. No. 6,166,183 teaches a pegylated human G-CSF, its production and uses.

The proteins or polypeptides referred to above may be administered in a suitable diluent. The diluent is selected so as not to affect the biological activity of the combination. Examples of such diluents are distilled water, physiological saline, Ringers solutions, dextrose solution, and Hank's solution. In addition, the pharmaceutical composition or formulation may also include other carriers, adjuvants, or nontoxic, nontherapeutic, nonimmunogenic stabilizers and the like.

Moreover, the said proteins or polypeptides may be co-administered with other therapeutics, such as standard medication, antimicrobials, monoclonal antibodies and other recombinant growth or development factors.

The term "antimicrobial" is meant to include therapeutic agents for the prophylaxis or treatment of diseases, disorders and/or complications associated with bacterial, fungal, viral, protozoal, or parasitical infections.

The term "a time sufficient to allow mobilization or release of the leukocytes" refers to the time which the leukocytes require to get activated by G-CSF and the time which they require to be mobilized and to enter the blood. Said time window may vary between different classes of subjects and also between different individuals of a class of subjects. However, the person skilled in the art can easily adopt the method of the invention without further ado.

The term "hematopoietic production and storage tissues and sites of margination" encompasses tissues and organs which are capable of producing, storing or harboring leukocytes. Said tissues or organs or sites comprise, inter alia, liver, bone marrow, spleen, lymphoid organs, lung, skin, vascular endothelium or the microcirculation.

The term "assessing" encompasses putting into relation the amount of leukocytes determined in step (a) of the method of the invention with the amount of leukocytes which have been mobilized or released in a control subject, wherein said control subject is known to have a defined risk for a disease, disorder or complication associated with high-dose cytotoxic chemotherapy and/or hematopoietic cell transplantation or a susceptibility therefor. Preferably, said assessment is achieved by comparing the said amounts of leukocytes or a statistic value derived therefrom. Suitable statistical values and the calculation thereof are well known in the art and comprise, inter alia, the median and distribution. Moreover, a detailed method how the assessment in accordance with the present invention can be carried out is described in the accompanied Examples. Most preferably, as shown in the accompanied Examples, assessment is carried out by comparing the determined amount of leukocytes with categorized control groups having a defined risk for the aforementioned diseases, disorders or complications or susceptibilities therefor.

The term "control subject" refer to subjects for which the hematopoietic cytocapacity has been established already by the method of the invention and for which the risk for a disease, disorder, complication or susceptibility therefor has been known from previous sources of risk estimation based on experience. The term "control group" means a group of control subjects which fit into the same risk category for a disease, disorder, complication or susceptibility therefor referred to in accordance with this invention.

The term "high risk", "intermediate risk" and "low risk" refers to differences in the individual predisposition for developing a disease, disorder, complication or susceptibility therefor, preferably after a subject has been treated by one of the therapies referred to below, such as high-dose chemotherapy. Said high, intermediate or low risk can be statistically analyzed. Preferably, the differences between a subject or a group of subjects having a high, intermediate or low risk are statistically significant. This can be evaluated by well known statistic techniques including Student's t-Test, $Chi^2$-Test, Wilcoxon-Mann-Whitney Test, Kurskal-Wallis Test or Fisher's exact Test, log-rank test, logistic regression analysis, or Cox models. Most preferably, the risk groups are analyzed as described in the accompanied Examples whereby explorative data analysis is carried out and the risk groups are formed with respect to the median, the 25% and the 75% percentiles. Based on this analysis, relative scale cut-off values for risk group formation can be defined. Within groups having received similar or identical chemotherapies, also the absolute leukocyte values can be used as cut-offs. The term "similar or identical chemotherapies" preferably means such chemotherapies where essentially the same degree of myelosuppression is achieved at essentially the same time point. Differences in continuous variables of the groups are tested by Wilcoxon-Mann-Whitney Test or Kurskal-Wallis Test depending on the number of groups to be compared. For nominal or ordered categories, Fisher's exact or $Chi^2$-Test for trend are applied. Without further ado, the person skilled in the art can carry out multivariant analysis with stratified versions of the aforementioned tests or Cox models in order to examine the independent impact of predictive factors and to establish the different risk groups.

The term "disease, disorder or complication associated with high-dose cytotoxic chemotherapy and/or hematopoietic cell transplantation or a susceptibility therefor" comprises those diseases, disorders or complications which have been reported to be caused by or are associated with the procedure. Preferably, such diseases, disorders or complications comprise those explicitly mentioned below.

Advantageously, it has been found in accordance with the present invention that a predictive value for the risk assessment for diseases, disorders or complications associated with high-dose cytotoxic chemotherapy and/or hematopoietic cell transplantation, can be generated due to determining the leukocyte peak which is generated by G-CSF in a subject which had been treated by cytotoxic chemotherapy. Within hours after G-CSF administration, leukocytes enter the circulation. In accordance with the present invention it has been observed that a leukocyte peak after a single dose of G-CSF given after high-dose therapy and after further autologous transplantation of peripheral blood stem cells (PBSCs) correlated with the hematopoietic recovery. Fluorescence in situ hybridisation (FISH) for XY chromosome on blood leukocytes in sex-mismatched allogeneic hematopoietic transplant recipients have demonstrated that the peripheral blood leukocytes at this early time after transplantation and under G-CSF administration are mainly of host, and not transplant origin (Arseniev 1997). To further exclude any contribution of the autograft to this phenomenon, G-CSF has been administered before autologous transplantation and it has been investigated whether the induced transient leukocyte peaks were a functional measure for the host hematopoietic capacity and would predict the hematopoietic recovery and related variables after high-dose cytotoxic chemotherapy.

The value of the early leukocyte peaks in the circulation upon a single dose of G-CSF following to high-dose chemotherapy predicted the duration and severity of neutropenia and leukopenia and the recovery rate of host hematopoiesis. The hematological parameters evaluated after the cytocapacity test are preferably one or more of the time to neutrophil and platelet recovery and also the duration of leukopenia <1000/μl, the duration of neutropenia <500/μl, and the residual neutrophil/leukocyte level in the blood during myelosuppression. Surprisingly, the correlations between the cytocapacity test and these hematological parameters known to be associated with morbidity and mortality from myelosuppression were highly significant. The cytocapacity test therefore appeared to provide a measure of the capacity of host hematopoiesis to overcome the effects of cytotoxic therapy. Preferably, at the time point of the cytocapacity test the blood cell counts still are normal or close to normal and the test result can advantageously be considered for the management of the time period of myelosuppression and/or the transplant.

The cytocapacity test may be used at a time point before, during, or after cytotoxic therapy. The cytocapacity test yields a prediction regarding the assessment of the possibility of a disorder, complication and/or disease. That prediction may advantageously be used in order to decide the stop of the therapy and/or modification of the treatment. Thus, after measuring very low cytocapacity test values, it may be decided that no (further) cytotoxic therapy and/or transplantation is administered. Alternatively, preferably when low to medium cytocapacity test values are measured, it may be decided that the therapy should be modified. For instance, the cytotoxic therapy may be modified, e.g. by reduction of the dose of one or more of the cytotoxic agents used therein, and/or by omission of at least one of such agents, and/or by changing to another protocol of selection of cytotoxic agents and/or dose and administration regimen thereof, such that the cytotoxic therapy has a less suppressive effect upon the patient's hematopoietic system. In addition, when a transplantation is administered, a higher number of CD34+ cells may be contemplated to be necessary in order to reconstitute the patient's hematopoietic system. Further alternatively or in addition, the transplantation of allogeneic or autologous hematopoietic stem cells may be considered, in order to (faster) reconstitute the patient's hematopoietic system. Still further, a standard antibiotic treatment usually given may be modified so as to include further antibiotics, different antibiotics, and/or higher doses of antibiotic treatment, in order to more effectively prevent and/or treat infection and the associated complication, disorder, disease and/or condition. The term "antibiotic" is to be understood herein to comprise substances effective against bacteria, parasites, protozoa, fungi and/or viruses.

When comparing leukocyte numbers obtained from different patients or patient groups, normalization of the values may be carried out. To this end, a relative scale may be used, so that only the relative increase in number is compared. Alternatively, or in combination, a categorization may be used, e.g., such as the categorization used in the Examples hereinbelow wherein the values are categorized in quartiles. In another embodiment of the invention, the normalization is carried out on the basis of the degree in myelosuppression achieved by cytotoxic chemotherapy and/or which is present in the patient and/or in the control subject. Using this kind of normalization, different patient groups with different degrees of myelosuppression at the time point of assessing cytocapacity may advantageously be compared.

With increasing time interval between the start of cytotoxic chemotherapy and single dose G-CSF, the median of the test-induced leukocyte peaks will be lower because of a decreasing availability of mature blood cells. There is, however, no impact of this on the rate of the hematopoietic recovery. To take this into account, the leukocyte peaks can be evaluated on a relative scale separately for groups of similar regimens. These relative values with respect to the median of the distribution constitute continuous cytocapacity test results as discussed, supra.

The cytocapacity test itself is independent from peripheral blood stem cell (PBSC) transplantation since the test is performed before the transfusion of the cryopreserved PBSCs. The transplantation of autologous PBSCs replenishes the chemotherapy-depleted progenitor cell pool. In multivariate analysis, the cytocapacity test was independent from the dose effect of PBSC CD34+ cells in prediction of the hematopoietic recovery.

The fast hematopoietic recovery with the use of mobilized PBSCs after high-dose chemotherapy (Beyer 1995; Schmitz 1996) and the associated good tolerability and low treatment-related mortality below 5% has spurred the interest in performing autografts on an outpatient basis (Meisenberg 1997; Herrmann 1999; Palumbo 1999). With a cytocapacity test >1.0 and when at least a standard dose of CD34+ cells (>2.5×10$^6$/kg) is transplanted, outpatient care as a possibility is suggested (see also Examples 3-5 hereinbelow). In this favorable group, there was an optimal neutrophil and platelet recovery, which was completed in 10 and 12 days, respectively. Therefore, in this group, the hematopoietic recovery occurred without delay and there was a significantly reduced risk of infection and a reduced requirement for antimicrobial therapy. Advantageously, with the availability of the cytocapacity test, the threshold CD34+ cell number required to be transplanted to achieve a favorable hematopoietic recovery can be determined. Neutropenic fever frequently is the first sign and hallmark of infection in cancer patients after cytotoxic chemotherapy. It is associated with a significant complication rate and usually leads to hospitalization and empiric broad-spectrum intravenous antimicrobial therapy as the standard of care (Pizzo 1993). Risk models incorporating a variety of clinical characteristics have been developed to define the complication risk for patients with neutropenic fever (Talcott 1992; Klastersky 2000). Low risk patients were candidates for empirical oral antimicrobial therapy (Kern 1999; Freifeld 1999) or outpatient treatment (Talcott 1994; Rubenstein 1993). Clearly, the intensity of chemotherapy is an important risk factor for neutropenic fever but also the individual susceptibility to acquire an infection. Low lymphocyte counts after chemotherapy were predictive for the occurrence of neutropenic fever (Blay, 1996). The neutrophil nadir after a first cycle of chemotherapy predicted subsequent neutropenia, chemotherapy dose reductions or treatment delays occurring in following cycles (Silber, 1998). The cytocapacity test, however, induces a rise in the blood leukocyte count prior to myelosuppression. In the investigation underlying the present invention, the cytocapacity test was the major predictor for the development of neutropenic fever, documented infection and the required intravenous antimicrobial therapy. Even when cases which had received ≦2.5× 10$^6$ CD34+ cells/kg and which therefore constitute an unfavorable group were excluded from the analysis, the observed continuous direct relation between the cytocapacity test and the absence of neutropenic fever and/or documented infection and the inverse relation with the requirement for antimicrobial therapy did not change. The cytocapacity test can provide the clinician with additional information regarding the risk of infection for an individual patient. The cytocapacity test also provides an instrument for risk stratification.

Based on the investigation underlying the present invention, the method of the present invention which can predict the hematopoietic recovery independently from the dose effect of transplanted CD34+ cells and can predict the risk of infection following high-dose cytotoxic chemotherapy has been established. Moreover, the cytocapacity test of the present invention can stratify the application and dose of hematopoietic growth factors, the CD34+ cell number to be transplanted, the intensity and duration of antimicrobial prophylaxis and therapy and the level of care for the myelosuppressed patient. Also encompassed by the invention is a cytocapacity test in different forms of myelo- or immunosuppression due to medical treatment, infection or primary and secondary bone marrow diseases or disorders. Therefore, according to the present invention, there is contemplated a method of prophylaxis of an infection in myelosuppressed subjects in general, by application of the cytocapacity test and determination of a suitable antimicrobial, antifungal, and/or antiviral therapy in accordance with the results of the cytocapacity test, optionally by considering further data about the general health or disease state of the patient and optionally, his relatives. The antifungal, antimicrobial, and/or antiviral therapy may be administered as preventive and/or therapeutical treatment. For instance, in the case of chronic infection, it may be decided that the patient is, based upon results of the cytocapacity test and optionally, further data about the general health or disease state of the patient and optionally, his relatives not able to effectively fight the infection. In consequence, a therapeutic treatment may be initiated.

Further, based upon a low results from the cytocapacity test, it may be decided to treat the hematopoietic and/or immune system of the patient, rather than treat an infection or prevent an infection by prophylaxis. To this end, the transplantation of hematopoietic stem cells, or the administration of hematopoietic growth factors, as single dose or as consecutive doses or as a long-term treatment, may be considered. One such hematopoietic growth factor is G-CSF. Other factors include Thrombopoietin, GM-CSF, Stem cell factor, Flt3 ligand, erythropoietin, KGF.

The present invention also relates to a method for selecting a suitable antimicrobial prophylaxis or therapy for a subject, wherein said method comprises the steps of the aforementioned method and the further step (c) selecting a suitable antimicrobial prophylaxis or therapy for said subject based on the results obtained in step (b).

The definitions and explanations of the terms made above apply mutatis mutandis.

The term "suitable antimicrobial prophylaxis or therapy" encompasses medical treatments which either prevent microbial infection effectively or which allow an efficient treatment thereof.

In an preferred embodiment of the invention said prophylaxis or therapy is a prophylaxis or therapy for the treatment, prevention or amelioration of an infection.

In an even more preferred embodiment of the invention said infection is selected from the group of fungal, viral, protozoal, parasitical and bacterial infections.

In a further preferred embodiment of the present invention the infection is selected from the group consisting of pneumonia, invasive fungal infection, enterocolitis, soft-tissue infection, and sepsis.

Said medical treatments may comprise the administration of antimicrobials or other substances, such as ciprofloxacin, amphotericin B, fluconazole, trimethoprim-sulfamethoxazole, acyclovir, piperacillin/tazobactam, gentamicin, meropenem, vancomycin or any combination administered simultaneously or subsequent of said antimicrobials or substances. Many other antimicrobials or substances could be administered. Also, cell preparations like granulocyte transfusions or others could be given. The dosage and schedule of such antimicrobials or other medical treatments depend on whether prophylaxis or therapy of microbial infections is to be achieved. Moreover, a clinician must also consider what infectious agents s/he has to expect and what infectious agents are isolated from the patient. A critical value for a suitable antimicrobial prophylaxis or therapy is the capability of the subject for hematopoietic recovery. These considerations have been made so far based on empirical data. Thanks to the present invention, the hematopoietic cytocapacity, as a critical landmark for hematopoietic recovery and the risk of infection in a subject, can be determined and allow to select a suitable prophylaxis and therapy without merely relying on empiric and average data.

Further, the present invention relates to a method for selecting a suitable prophylaxis or therapy for neutropenic fever for a subject, wherein said method comprises the steps of the aforementioned method and the further step (c) selecting a suitable prophylaxis or therapy for neutropenic fever based on the results obtained in step (b).

The definitions and explanations of the terms made above apply mutatis mutandis. The term "suitable prophylaxis or therapy for neutropenic fever" encompasses medical treatments which either prevent neutropenic fever effectively or which allow an efficient treatment thereof. Said medical treatments may use oral or intravenous administration of single or combinations of antimicrobials or biological humoral or cellular therapies. Preferably, a suitable prophylaxis or therapy for neutropenic fever involves administration of recombinant growth and development factors or cytokines like G-CSF and others as single or combination treatment in different dosage and schedule. Most preferably, said recombinant growth and development factors or cytokines are administered prophylactically. A critical value for a suitable prophylaxis or therapy of neutropenic fever is the capability of the subject for hematopoietic recovery. These considerations have been made so far based on empirical data.

Thanks to the present invention, the hematopoietic cytocapacity, as a critical landmark for hematopoietic recovery and the risk of infection in a subject, can be determined and allow to select a suitable prophylaxis and therapy of neutropenic fever without merely relying on empiric and average data.

Furthermore, the present invention relates to a method for selecting a suitable amount of hematopoietic stem cells, preferably $CD34^+$ cells to be transfused for the therapy of a subject, wherein said method comprises the steps of the method of claim 1 and the further step (c) of selecting the amount of said cells to be transfused for the therapy of a subject based on the results obtained in step (b).

The definitions and explanations of the terms made above apply mutatis mutandis.

The term "a suitable amount of hematopoietic stem cells, preferably $CD34^+$ cells for the therapy" refers to an amount of said cells which allows efficient hematopoietic recovery.

Also, the present invention relates to a method for selecting a suitable amount of a hematopoietic growth factor or cytokine for the treatment of a subject, wherein said method comprises the steps of the aforementioned method and the further step (c) selecting a suitable amount of a hematopoietic growth factor or cytokine for the treatment of said subject based on the results obtained in step (b).

The definitions and explanations of the terms made above apply mutatis mutandis. The term "a suitable amount of a hematopoietic growth factor or cytokine" refers to an amount of a hematopoietic growth factor which supports efficient hematopoietic recovery. Preferably, said hematopoietic growth factor is G-CSF, or other factors like GM-CSF, erythropoietin, stem cell factor, thrombopoietin or KGF. More preferably, a suitable dose of G-CSF is about 5 µg/kg per day applied subcutaneously.

The methods of the present invention encompass in vitro applications.

The present invention also comprises a method for determining the hematopoietic cytocapacity of a subject comprising the steps of:

(c) determining a parameter, preferably a parameter of a sample, preferably a body fluid, preferably blood or a blood derived sample, wherein the parameter is preferably a marker of a population or sub-population of cells, preferably hematopoietic cells, in said sample obtained from a mammal, wherein said mammal has been subjected to administration of a single dose of a hematopoietic growth factor, preferably G-CSF, and has been maintained for a time sufficient to allow mobilization or release of leukocytes from hematopoietic production and storage tissues and sites of margination into the blood; and (d) determining the hematopoietic cytocapacity by assessing the value of the parameter determined in step (a) with the value of the parameter measured in a like manner in a control mammal wherein said control mammal is selected from the group consisting of mammals having (i) a high risk for a disease, disorder or complication associated with high-dose cytotoxic chemotherapy and/or hematopoietic cell transplantation, (ii) an intermediate risk for a disease, disorder or complication associated with high-dose cytotoxic chemotherapy and/or hematopoietic cell transplantation or (iii) a low risk for a disease, disorder or complication associated with high-dose cytotoxic chemotherapy and/or hematopoietic cell transplantation.

Even more preferred said mammal is a human. Further preferred, said marker is a T cell associated marker, or a B cell associated marker. Markers within the ambit of the present invention are specified, e.g, in Example 7.

Finally, the present invention encompasses a method of treating a disease, disorder or complication associated with high-dose cytotoxic chemotherapy and/or hematopoietic cell transplantation or a susceptibility therefor in a subject as specified herein comprising the steps of the methods specified herein and the further step of administering to said patient (i) a suitable antimicrobial prophylactic or therapeutic agent in an effective amount, (ii) a suitable agent for the prophylaxis or therapy of neutropenic fever in an effective amount, (iii) an effective amount of hematopoietic stem cells, preferably $CD34^+$ cells, or (iv) an effective amount of a hematopoietic growth factor.

The definitions and explanations of the terms made above apply mutatis mutandis. The dosage regimen for said administration of an agent, cells or growth factor will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

Encompassed by the present invention is the use of leukocytes obtained from a subject for the preparation of a diagnostic composition for diagnosing a susceptibility for a disease, disorder or complication associated with high-dose cytotoxic chemotherapy and/or hematopoietic cell transplantation in said subject, wherein said subject has been subjected to administration of a dose of G-CSF and has been maintained for a time sufficient to allow mobilization or release of the leukocytes from hematopoietic production and storage tissues and sites of margination into the blood.

The definitions and explanations of the terms made above apply mutatis mutandis.

The term "diagnostic composition" as used in accordance with this invention refers to an entity of the leukocytes obtained from the said subject which allow determination of a therapeutic or prognostic value of said leukocytes, preferably their absolute or relative number in a given volume of blood. Dependent on the method of determination of the number of leukocytes, said cells may be pretreated, e.g., for fluorescence activated cell sorting (FACS) analysis or may be applied to a suitable counting device such as a counting slide. Such pretreatment measures are well known in the art.

In light with the foregoing, in a preferred embodiment of the method or the use of the invention said disease, disorder or complication associated with high-dose cytotoxic chemotherapy and/or hematopoietic cell transplantation, is neutropenic fever, microbial infection, delayed hematopoietic recovery, bleeding, immunosuppression, immunological effects directed against the host, high level of supportive care, morbidity and mortality.

In another preferred embodiment of the method or the use of the invention said subject is a human.

In a furthermore preferred embodiment of the method or the use of the invention said subject has been subjected to high-dose chemotherapy.

The term "high-dose chemotherapy" refers to the dosage and intensity of chemotherapy which is regarded as "high-dose" when a significant myelosuppression follows with significantly reduced peripheral blood leukocyte and platelet counts and an increased risk of infection. Depending on the dosage of the chemotherapeutic substances, a transplantation of PBSCs may be required or not. Frequently, G-CSF or GM-CSF are applied after high-dose chemotherapy and transfusions of red blood cells or platelets are required.

Most preferably, said high-dose chemotherapy comprises administration of melphalan, busulfan, cyclophosphamide, carmustine, etoposide and cytarabine or other chemotherapeutic substances. In the high-dose chemotherapy, escalated dosages can be applied. High-dose regimens can consist of a combination of substances in escalated dosages with substances in conventional dosages. For additional immunosuppression in high-dose chemotherapy anti-thymocyte globulin (ATG) or anti-lymphocyte globulin (ALG) could be included in the regimens.

In another more preferred embodiment of the method or the use of the invention said subject has been subjected to myelosupressive chemotherapy.

The term "myelosupressive chemotherapy" refers to the effect of the chemotherapy on the bone marrow functions. A chemotherapy is myelosuppressive when the peripheral blood leukocyte counts and possibly platelet counts decrease for a limited period of time and recover thereafter spontaneously or under hematopoietic growth factor stimulation. Depending on the degree of myelosuppression there can be an increased risk of infection.

Most preferably, said myelosupressive therapy comprises the administration of cyclophosphamide, etoposide, carmustine, cytarabine, melphalan, busulfan, doxorubicin, epirubicin, paclitaxel, docetaxel, thiotepa, fludarabine, vincristine, bendamustine, cisplatin, carboplatin, daunorubicin, fluorouracil, gemcitabine, idarubicin, ifosfamide, irinotecan, methotrexate, mitoxantrone, oxaliplatin, treosulfan, vinblastine, vinorelbine. Other chemotherapeutic substances could be administered as well.

In a furthermore preferred embodiment of the method or the use of the invention said subject has been subjected to radiotherapy, suffers from a primary or secondary bone marrow disease, an autoimmune disease, a hereditary disease or disorder or an infection.

The term "radiotherapy" refers to any therapeutic application of ionic radiation. Said radiation may be radioactive radiation including fast electrons, neutrons, protons, or Pi-mesons, microwaves, IR, and UV radiation. Preferably, said radiation is used to treat cancer or malignant hematopoietic diseases.

The term "primary bone marrow disease" encompasses those diseases and disorders which primarily effect the cells of the bone marrow. Examples for said diseases or disorders are acute or chronic leukemias, myelodysplasia, aplastic anemia, congenital neutropenia, cyclic neutropenia, idiopathic and autoimmune neutropenia.

The term "secondary bone marrow disease" encompasses those diseases and disorders where the bone marrow becomes involved secondarily like in case of bone marrow metastases of a cancer.

The term "autoimmune disease" refers to those diseases which are associated with the presence of autoantibodies in a patient. Examples for said diseases or disorders are rheumatoid arthritis or lupus erythematosus.

The term "hereditary disease or disorder" encompasses all diseases or disorders which are caused by genetic defects that will be transmitted via the germ line. Most preferably, said hereditary disease or disorder within the scope of this invention is cyclic neutropenia, Kostmann syndrome, Shwachman syndrome and Gaucher's disease.

The term "infection" preferably encompasses those infections which can result in life-threatening conditions for the subject. Infections can lead to serious, organ dysfunction and organ failure in the myelosuppressed host. Such infections can be caused by bacteria, viruses, fungi, protozoa and parasites like staphylococci, streptococci, enterococci, *escherichia coli, klebsiella* species, *Pseudomonas aeruginosa, candida* species, *Aspergillus* species, *Pneumocystis carinii*, cytomegalovirus, herpes viruses, respiratory viruses and many other microbials. It is understood by the person of skill in the art that with a myelosuppressed patient, any infection may potentially be life-threatening. However, it is further to be understood that by the present invention there are also contemplated embodiments where the infection that is to be treated, ameliorated and/or prevented may not be life-threatening or may not lead to life-threatening conditions. Nevertheless, application of the cytocapacity test in a subject may lead the attending physician to consider treatment, prevention and/or amelioration of any such infection.

In accordance with the aforesaid, the invention provides a method for determining the hematopoietic cytocapacity of a subject comprising the steps of:
  (a) determining the amount of leukocytes present in a blood sample obtained from a subject, wherein said subject has been subjected to administration of a single dose of G-CSF and has been maintained for a time sufficient to allow mobilization or release of the leukocytes from hematopoietic production and storage tissues and sites of margination into the blood; and
  (b) determining the hematopoietic cytocapacity by assessing the amount of leukocytes determined in step (a) with the amount of leukocytes which have been mobilized or released in a control subject.

The invention preferably provides the above method further comprising a step (c) wherein (c) comprises selecting a suitable antimicrobial prophylaxis or therapy, or hematopoietic growth factor treatment, for said subject based on the results obtained in step (b).

The above control subject may be a healthy control subject. Preferably, the control subject is selected from the group consisting of subjects having (i) a high risk for a disease, disorder or complication associated with high-dose cytotoxic chemotherapy and/or hematopoietic cell transplantation, (ii) an intermediate risk for a disease, disorder or complication associated with high-dose cytotoxic chemotherapy and/or hematopoietic cell transplantation or (iii) a low risk for a disease, disorder or complication associated with high-dose cytotoxic chemotherapy and/or hematopoietic cell transplantation.

In another more preferred embodiment of the method or the use of the invention said G-CSF is filgrastim (Neupogen™; Amgen Inc., Thousand Oaks, Calif., USA) or lenograstim (Granocyte™; Chugai, Japan).

Said G-CSF preparations are commercially available and have been approved from the drug regulation administrations for the purpose of medical treatments. Thus, application of said preparations is preferred for the methods and uses of this invention.

Preferably, said dose of G-CSF is selected from a range of about 1 to about 100 μg/kg body weight of the said subject. More preferably, the dose of G-CSF is selected from a range of about 1 to about 20 μg/kg body weight of the said subject.

Also more preferably, said dose of G-CSF is 1.0, 2.5, 5, 7.5, 10 or 15 μg/kg body weight of the said subject Further preferably, the dose of G-CSF is selected from a range of about 15 to about 30, 60 and about 100 μg/kg body weight of the said subject. Still further preferably, the dose of G-CSF is selected from a range of about 20 to about 30, 60 and about 100 μg/kg body weight of the said subject. Without being bound by theory, it is the belief of the inventors that higher doses of G-CSF (about 15 μg/kg body weight of the said subject or more) lead to more pronounced differentiation of the patients and therefore may improve the predictive value of the cytocapacity test. This may especially be true for patients that have not undergone high-dose treatment or for healthy subjects. If alternative dosing, e.g., based on the body surface area is used, similar absolute amounts of G-CSF are intended.

In a more preferred embodiment of the method or the use of the invention said time sufficient to allow mobilization or release of the leukocytes is in the range of 1 to 120 hours.

Also more preferably, said time sufficient to allow mobilization or release of the leukocytes is at least 1 hour, at least 2 hours, at least 6 hours, at least 10 hours, at least 12 hours, at least 14 hours or at least 18 hours.

Several documents are cited throughout the text of this specification. Full bibliographic citations may be found at the end of the specification immediately preceding the claims. Each of the documents cited herein (including any manufacturer's specifications, instructions, etc.) is hereby incorporated by reference.

The Figures show:

FIG. 1: Leukocyte peak after single dose G-CSF and leukocyte course. The G-CSF-induced leukocyte peak was observed (day 0) in a patient with multiple myeloma of this seris who received high-dose melphalan treatment. Autologous PBSC transplantation was performed approximately 1 hour after the leukocyte peak measurement. HDT, high-dose chemotherapy.

Figure 2:
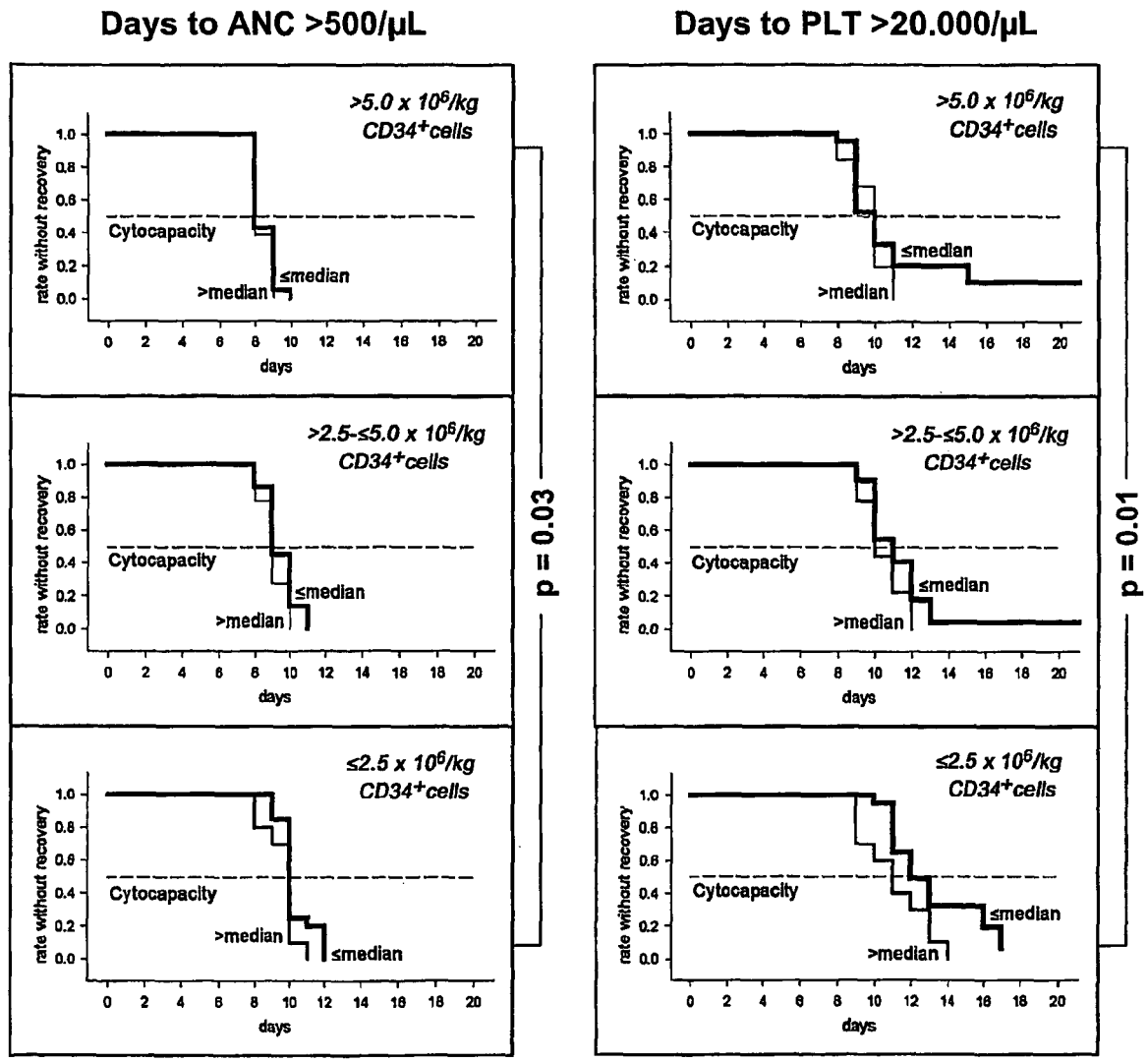

FIG. 2: The independence of the cytocapacity test from the $CD34^+$ cell number in the prediction of the neutrophil and platelet recovery. The kinetics of the neutrophil (absolute neutrophil count, ANC) (left) and platelet (PLT) recovery (right) are shown for separated $CD34^+$ cell levels. Within the respective $CD34^+$ cell level, a stratification for the cytocapacity test (≦median, >median) was performed. A stratified log-rank test was used to investigate the independent prediction of the hematopoietic recovery by the cytocapacity test over the three indicated $CD34^+$ cell levels.

Figure 3:
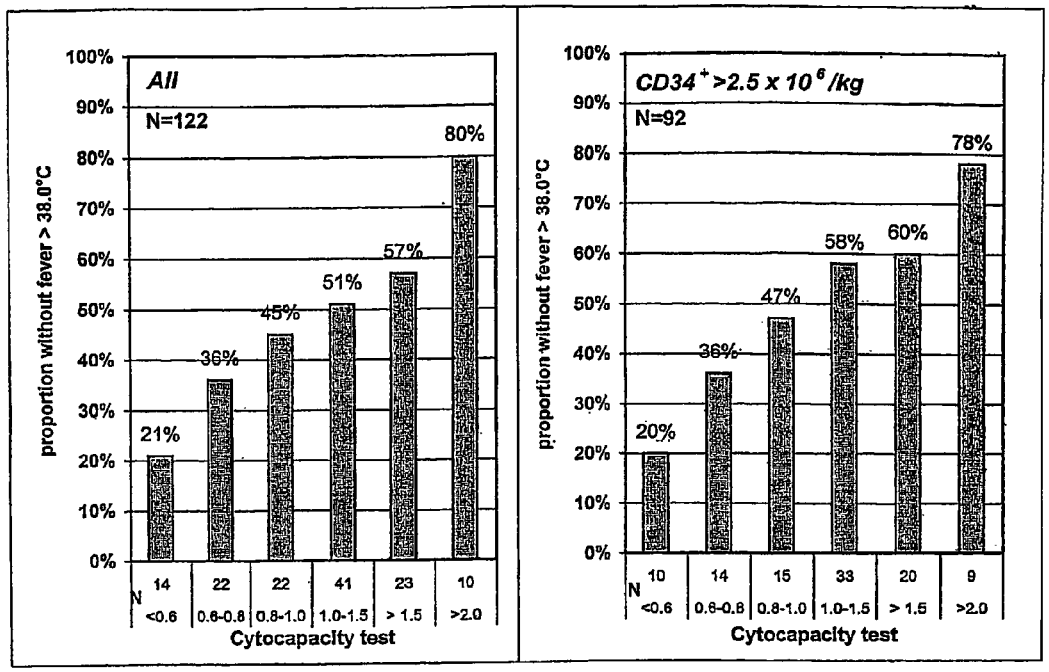
Figure 3:
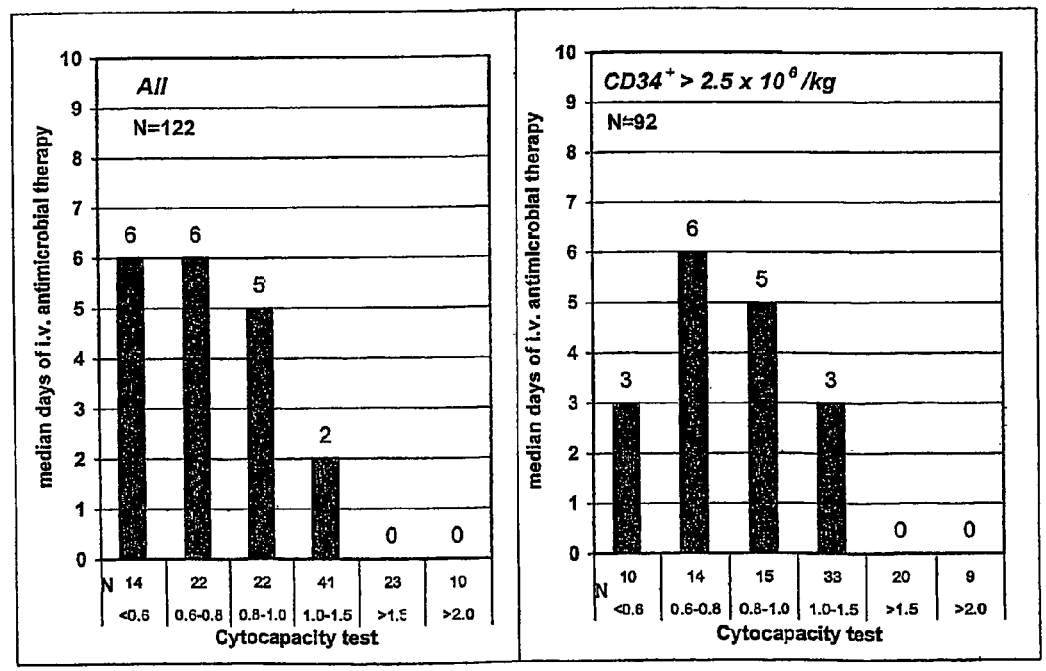

FIG. 3: Prediction of fever >38.0° C. and of antimicrobial therapy by the cytocapacity test. The categories of the cytocapacity test are based on the established relative scale where the median of the leukocyte peak distribution was set as 1.0. The proportion of cases within the categories without fever >38.0° C. (A) and the corresponding median days of intravenous antimicrobial therapy (B) are presented. On the left side, the data is shown for the entire number of cases, on the right side cases which had received a CD34+ cell number $\leq 2.5 \times 10^6$/kg were excluded.

Figure 4:
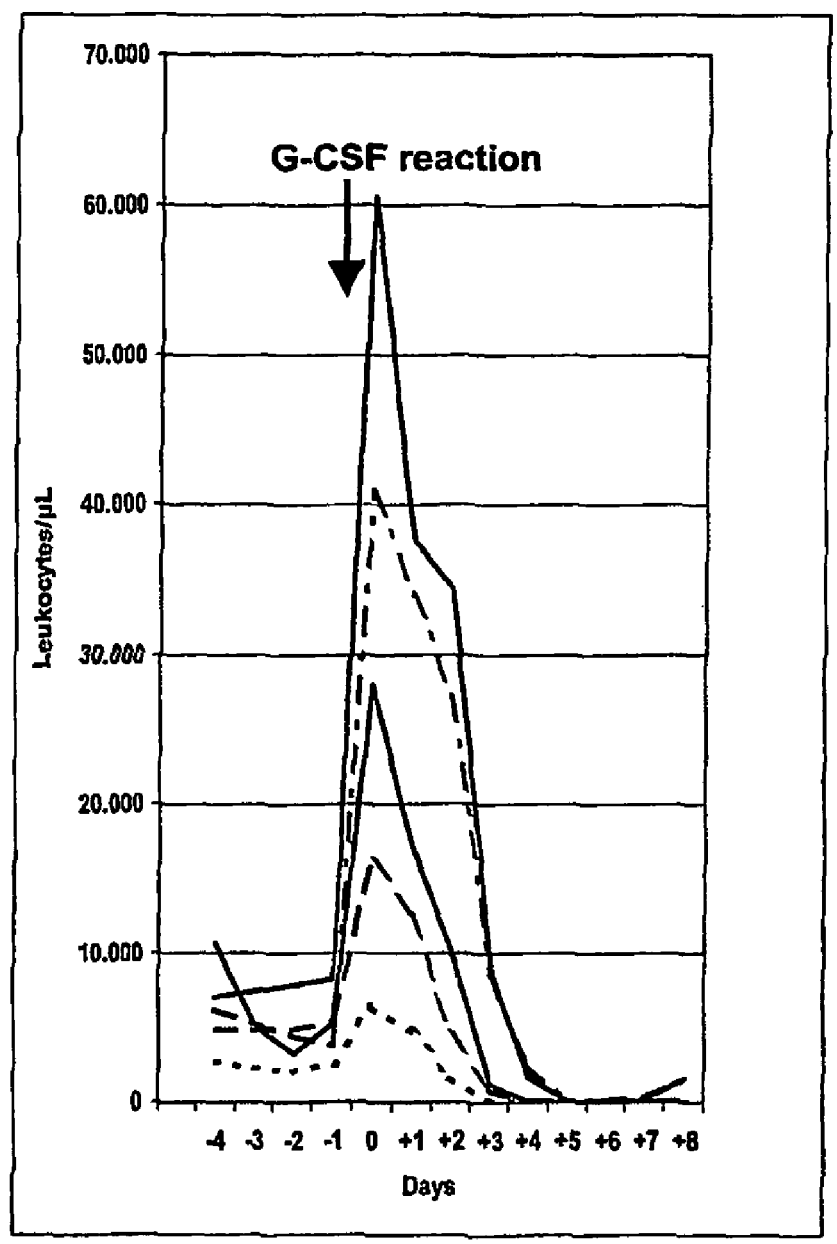

FIG. 4: The release of the G-CSF reaction. A single dose of G-CSF (5 µg/kg) was given approximately 30 hours after the completion of high-dose chemotherapy. The induced leukocyte peak which is shown for 5 different patients was measured after 12-14 hours. The autologous blood stem cell transplantation was performed afterwards.

Figure 5:
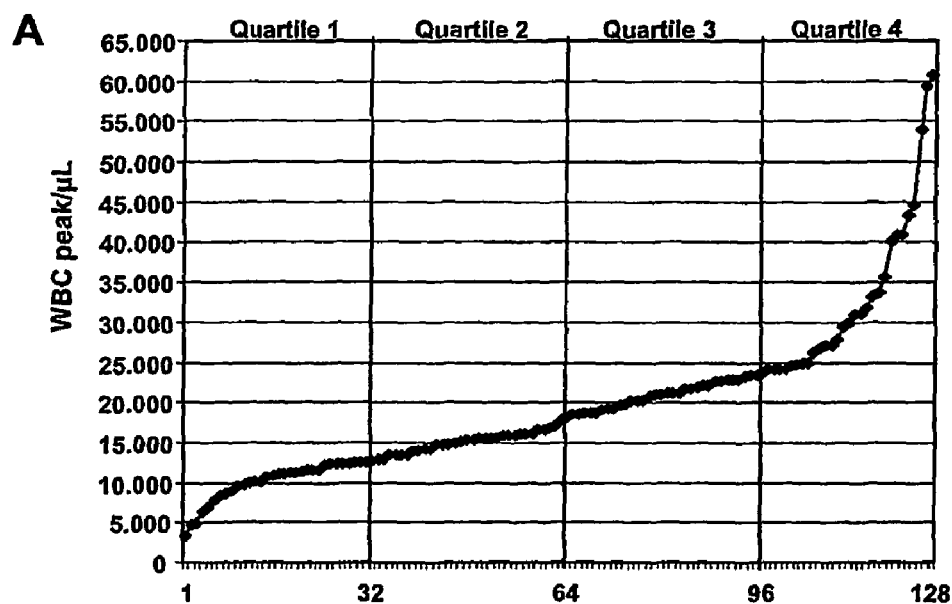
Figure 5:
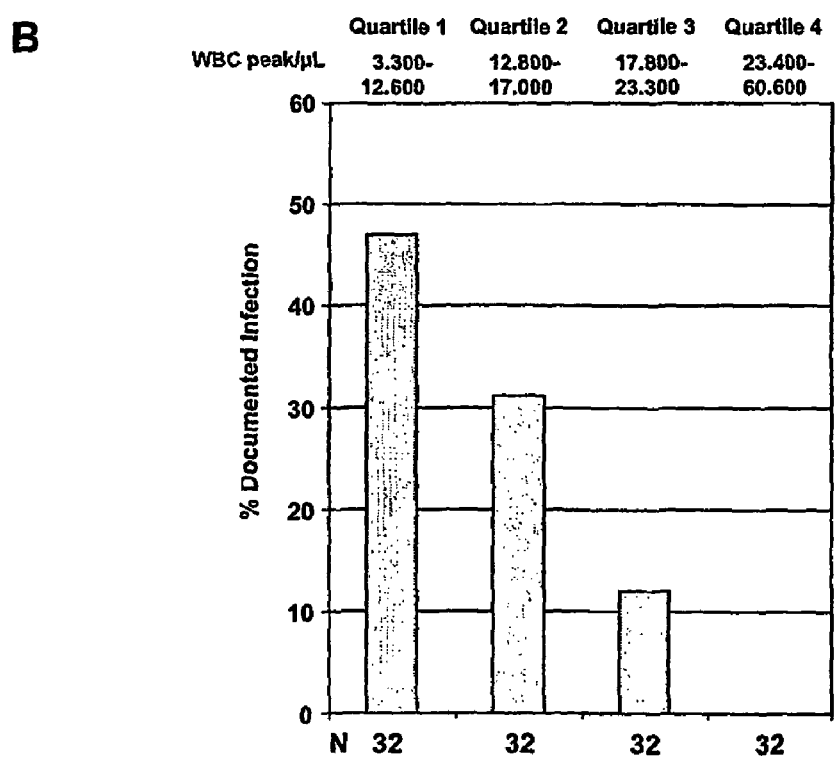

FIG. 5: Distribution of WBC peaks representing the G-CSF reaction ordered according to magnitude (A) and correlation of the G-CSF reaction with the rate of documented infections (B).

The present invention is illustrated by reference to the following biological Examples which are merely illustrative and are not to be constructed as a limitation of the scope of the present invention.

EXAMPLE 1

The Cytocapacity Test

Patients

Eighty-seven patients with multiple myeloma (MM) and relapsed non-Hodgkin's lymphoma (NHL) or Hodgkin's disease (HD) received high-dose therapy with standard regimens (Philip 1995; Barlogie 1997; Weaver 1998; Linch 1993, Palumbo 1999) followed by a single dose of G-CSF before autologous peripheral blood stem cell (PBSC) transplantation at one institution. The patients gave informed consent. The characteristics of the patients are presented in table 1.

PBSC Mobilization, Harvesting, Processing and Cryopreservation

In the vast majority of patients, the IEV regimen with G-CSF was used for mobilization. The IEV regimen consists of ifosfamide 2500 mg/m$^2$ intravenously day 1-3, epirubicin 100 mg/m$^2$ intravenously day 1 and etoposide 150 mg/m$^2$ intravenously day 1-3 followed by G-CSF (filgrastim; Amgen, Thousand Oaks, Calif., USA) at a dose of 5 µg/kg subcutaneously daily from day 5 until the completion of PBSC harvesting. Apart from individual dose reductions, patients with MM at an age $\geq 60$ years received IEV in a 75% dosage since 2000. PBSCs were harvested when the post-nadir, G-CSF stimulated leukocyte count rose up to 5000-10000/µL or above using a COBE Spectra (COBE, Heimstetten, Germany) or an AS104 (Fresenius, St. Wendel, Germany) cell separator and standard programs. In 20 patients (23%) with MM or low-grade NHL, harvested PBSC from a single leukapheresis underwent immunomagnetic B cell purging (MaxSep, Baxter Immunotherapy, Unterschleissheim, Germany) immediately after the collection. The PBSCs were mixed with an equal volume of a freezing solution which was prepared with 5% HSA and 100% DMSO (Cryoserv, Tera Pharmaceuticals, Midvale, Utah, USA) (4:1). The final DMSO concentration was 10%. After computerized controlled-rate freezing, the bags containing the PBSCs were stored in the vapor phase of liquid nitrogen.

CD34+ Cell Enumeration and PBSC Dose

The determination of CD34+ cells was carried out according to the guidelines of ISHAGE (Sutherland 1993) using a FACScan (BD, Mountain View, Calif., USA) or an EPICS XL-MCL (Electronics, Miami, Fla., USA) flow cytometer equipped with an argon laser. Whole blood was incubated for 30 minutes at 4° C. in the dark with the PE conjugated monoclonal anti-CD34 antibody and the FITC conjugated monoclonal anti-CD45 antibody followed by a wash and red blood cell lysis (BD). Before 1998, 20000 cells were analysed, 75000 cells thereafter. To exclude cell debris, platelets, remaining red cells and all CD45 negative cells, a forward scatter versus CD45 fluorescence dot plot was used. The double-positive CD34+/CD45+ cell population was then defined and backgated for low CD45 expression and low side scatter properties. The percentage of the so defined CD34+ cells was multiplied with the total nucleated cell content of the apheresis product to result in the absolute number of CD34+ cells harvested. The nucleated cell content was determined by automated cell counting using a Coulter STKS (Coulter, Miami, Fla., USA). The anti-CD34 antibody (HPCA-2), the anti-CD45 antibody (2D1) and the isotype controls used were from BD.

High-dose Therapy and Autotransplantation

Fifty-eight patients with MM (67%) were either treated according to the "Total Therapy" concept of Barlogie (Barlogie 1997) and were to receive tandem melphalan 200 mg/m$^2$ (MEL200) within 3-6 months or at an age between 60 and 70 years were treated with tandem melphalan 100 mg/m$^2$ (MEL100) according to Palumbo (Palumbo 1999). The younger patients with MM who did not reach a partial remission after a first melphalan 200 mg/m$^2$ were to receive busulfan 12-16 mg/kg and cyclophosphamide 120 mg/kg as second high-dose treatment (BUCY). Twenty-nine patients with relapsed NHL or HD (33%) were treated either with busulfan 16 mg/kg and cyclophosphamide 120 mg/kg (BUCY) or with carmustine 300 mg/m$^2$, etoposide 800 mg/m$^2$, cytarabine 800 mg/m$^2$ and cyclophosphamide 140 mg/kg (BEAC) (Philip 1995) or with carmustine 300 mg/m$^2$, etoposide 800 mg/m$^2$, cytarabine 1600 mg/m$^2$ and melphalan 140 mg/m$^2$ (BEAM) (Linch 1993). The distribution of high-dose regimens is shown in table 1. Autologous PBSC transplantation was performed 48-60 hours after the last dose of chemotherapy. The PBSC products were thawed in a 37° C. water bath at the bedside and were reinfused through a central venous catheter after the addition of 20 mL ACD-A.

Application of G-CSF and Blood Cell Counts

G-CSF was always given more than 24 hours after the last chemotherapy infusion, as recommended (Ozer 2000). The recombinant human G-CSF given subcutaneously after high-dose chemotherapy was filgrastim (Amgen, Thousand Oaks, Calif., USA) in 113 cases and lenograstim (Chugai, Japan) in 9 cases. The single G-CSF injection evaluated was given on the evening before PBSC autograft at a dose of 5 µg/kg. The induced leukocyte peaks were detected with the routine blood tests on the next morning, approximately 14 hours after the single G-CSF dose. The transplantation of autologous PBSCs was carried out approximately 1 hour after the routine blood test. From the day after PBSC transplantation, G-CSF was given daily at a dose of 5 µg/kg until leukocyte counts were between 5000/µL and 10000/µL following aplasia. Routine blood cell counts including a differential were performed on a Coulter STKS (Coulter, Miami, Fla., USA) daily from the start of high-dose therapy until the patients left the hospital.

Supportive Care

All the patients were hospitalized during high-dose therapy, autograft and the post-transplant phase. The antimicrobial prophylaxis consisted of the following: From the time of autograft until neutrophil recovery ciprofloxacin 2×250 mg daily was given. Oral amphotericin B suspension 4×1 mL was given during the entire hospital stay or, alternatively, in case of oral amphotericin intolerance, oral fluconazole 1×100 mg daily. *Pneumocystis carini* pneumonitis prophylaxis was started during the administration of high-dose chemotherapy with trimethoprim/sulfamethoxazole 160 mg/800 mg 2×1 daily and was continued after neutrophil recovery with 2×1 on two consecutive days per week for 6 months. In case of trimethoprim/sulfamethoxazole intolerance, alternatively a pentamidin inhalation with 300 mg was performed every 4 weeks for 6 months from autograft. Intravenous acyclovir was given at a dose of 2×500 mg from the start of high-dose therapy until neutrophil recovery. Red blood cell products and single-donor platelets were substituted to maintain a hemoglobin level above 80 g/L and a platelet count above 10000/µL. All blood cell products were CMV negative, were irradiated with 30 Gy and were transfused through a leukocyte reduction filter. Empirical intravenous antimicrobial therapy was started during neutropenia after a single oral temperature >38.5° C. or when fever >38.0° C. was present over at least one hour and was carried out according to previously published guidelines (Hughes 1997). The initial treatment was carried out with piperacillin/tazobactam plus gentamicin. Escalation was performed with meropenem/vancomycin. If fever persisted on days 5-7, intravenous amphotericin B was added. The antimicrobial treatment was continued until neutrophil recovery and at least 24 hours after the resolution of fever. Patients were discharged from the hospital after neutrophil and platelet recovery and after the cessation of antimicrobial therapy.

Assessment of Hematopoietic Recovery, Fever and Supportive Care

Neutrophil recovery was defined as the first day with a neutrophil count above 500/µL from the day of autograft. Platelet recovery was defined as the first day with an unsubstituted platelet count above 20000/µL from the day of autograft. The occurrence of fever >38.0° C., the number of days with fever >38.0° C. and the days with intravenous antimicrobial therapy were recorded until the patients were discharged from the hospital.

Objectives and Statistical Analysis

The objectives of this investigation were to correlate the G-CSF-induced leukocyte peak with the neutrophil and platelet recovery, the incidence of neutropenic fever and the duration of intravenous antimicrobial therapy and to compare these correlations with those obtained for the $CD34^+$ cell content of the PBSC autograft. All analyses presented (except for the demographic and disease baseline characteristics) are based on transplantation courses as units of observation.

The rates of neutrophil and platelet recovery over time were estimated using the product-limit method according to Kaplan and Meier (1958) and prognostic subgroups were compared by use of the log-rank test (Peto 1972). Differences in continuous variables between prognostic groups were tested by Wilcoxon-Mann-Whitney or Kruskal-Wallis analysis, depending on the number of groups. In case of nominal or ordered categories, Fisher's exact or $chi^2$ tests for trend were applied. Multivariate analysis was carried out with stratified versions of the respective tests or Cox models (Cox 1972) in order to examine the independent impact of the predictive factors with regard to the different end-points. All reported p-values result from two-sided tests.

Performance of the Cytocapacity Test

A single subcutaneous G-CSF injection (5 µg/kg) was investigated following 122 high-dose chemotherapy courses in 87 patients with multiple myeloma or lymphoma. The induced peripheral blood leukocyte peaks were detected with the routine blood tests approximately 14 hours later. These leukocyte peaks (FIG. 1) consisted of around 90% neutrophils. The patient and treatment characteristics are presented in table 1, the induced leukocyte peaks, the neutrophil and platelet recovery, the absence of fever >38.0° C. and the requirements for intravenous antimicrobial therapy in table 2. The time interval between the start of intravenous chemotherapy and the single G-CSF injection had an effect on the median of the induced leukocyte peaks. The oral administration of busulfan for 4 days in the BUCY regimen, however, which preceded the 2 day-intravenous administration of cyclophophamide, did not reduce the leukocyte peaks compared to the MEL regimen with a 2 day-intravenous administration of melphalan.

In case of BUCY and MEL high-dose therapy, with a 2.5 day-interval between the start of intravenous chemotherapy and single dose G-CSF, the median leukocyte peak was 16200/µL. In case of BEAM and BEAC high-dose therapy, with a 6.5 day-interval, the median leukocyte peak was 4100/µL, which was a factor 4 lower. The observed objectives of this analysis, however, were comparable between the BUCY/MEL and the BEAC/BEAM group (table 2). This suggested to evaluate the leukocyte peaks on a relative scale which was defined by the median (set as 1.0) of the distribution and was applied on the BUCY/MEL and the BEAC/BEAM group. For statistical analysis, categorizations of the leukocyte peak values in below ($\leq$50. percentile) and above (>50. percentile) the median and subsequently into $\leq$25. percentile, >25.-$\leq$50. percentile and >50. percentile were used. The entire median-orientated values on the relative scale corresponding to the minimum, 25. percentile, 50. percentile and maximum were 0.15, 0.77, 1.0 and 3.66, respectively. The test is termed cytocapacity test.

EXAMPLE 2

Prediction of the Hematopoietic Recovery

The median time to neutrophil (>500/µL) and platelet (>20000/µL) recovery was 9 and 10 days, respectively. The cytocapacity test predicted the neutrophil (p=0.001) and the platelet recovery (p<0.0001) (table 3). Interestingly, for the leukocyte counts before the test, a borderline significant correlation with the neutrophil recovery (p=0.06) but no correlation with the platelet recovery (p=0.4) was found. The number of $CD34^+$ cells in the autologous PBSC graft also predicted the neutrophil (p<0.0001) and platelet recovery (p<0.0001) (table 3), as expected.

The cytocapacity test itself was independent from the PBSC autograft since the test was performed before the cryopreserved autologous PBSCs were transfused. The correlation between the induced leukocyte peaks and the $CD34^+$ cell number was weak (r=0.226; p=0.01). In multivariate analysis, performed as a stratified log-rank test, the independent impact of the cytocapacity test (<=median, >median) in the prediction of the neutrophil (p=0.03) and the platelet recovery (p=0.01) could be followed through the different CD34 levels, increased with a lower $CD34^+$ cell number and modified the $CD34^+$ cell dose effect of the PBSC autograft. In a Cox model where the $CD34^+$ cell number of the autograft was included as a quantitative variable, the independent impact of the cytocapacity test on the neutrophil (p=0.05) and platelet recovery (p=0.0007) was confirmed.

EXAMPLE 3

Determination of a Favorable CD34+ Cell Threshold for Transplantation

The cytocapacity test itself was independent from PBSC transplantation since the test was performed before the transfusion of the cryopreserved PBSCs. In multivariate analysis, the cytocapacity test independently from the dose effect of the PBSC CD34+ cells predicted the hematopoietic recovery. This could have practical consequences for choosing a threshold dose of CD34+ cells for transplantation. With a cytocapacity test >1.0, the transplantation of >2.5×10$^6$ CD34+ cells/kg was sufficient to achieve a favorable neutrophil and platelet recovery, completed in 10 and 12 days, respectively. In cases with a cytocapacity test <1.0, the increased risk for a delayed hematopoietic recovery would suggest to use a higher number of CD34+ cells.

EXAMPLE 4

Prediction of Neutropenic Fever and Intravenous Antimicrobial Therapy

Fever >38.0° C. was absent in 55 of 122 procedures (45%). The median number of days with fever >38.0° C. was one day and intravenous antimicrobial therapy was given for a median of 4 days. The cytocapacity test was correlated with the absence of fever ($p=0.03$) and the median duration of intravenous antimicrobial therapy ($p=0.03$) (table 3). The search for a correlation of the CD34+ cell number in the PBSC autograft with the absence of fever >38.0° C. showed a trend ($p=0.07$) but no correlation with intravenous antimicrobial therapy was found ($p=0.3$). Both the cytocapacity test and the CD34+ cell number correlated with the duration of leukopenia <1000/μL ($p<0.0001$) whereas only the cytocapacity test correlated with the severity of leukopenia ($p=0.02$). A continuous direct relation between the cytocapacity test and the absence of fever and an inverse relation with the requirements for intravenous antimicrobial therapy was observed (FIG. 3). For the subgroup with a low cytocapacity test <0.6, the absence of fever was only 21% whereas for the subgroup with a high cytocapacity test >2.0 the absence of fever was 80%. The exclusion of cases which had received a PBSC autograft with a low CD34+ cell number (<=2.5×10$^6$/kg) and which therefore represent an unfavorable group from the analysis did not change this correlation (FIG. 3). Three treatment-related deaths occurred. These were caused by sepsis. The cytocapacity test in the three treatment-related deaths was 0.15, 0.77 and 1.0.

EXAMPLE 5

The Possibility of Outpatient Care

The fast hematopoietic recovery with the use of mobilized PBSCs after high-dose chemotherapy and the associated good tolerability and low treatment-related mortality below 5% has spurred the interest in performing autografts on an outpatient basis. With a cytocapacity test >1.0 in combination with a standard dose of CD34+ cells (>2.5×10$^6$/kg), outpatient care as a possibility was suggested. This constellation was associated with an optimal hematopoietic recovery (FIG. 2) and a reduced risk of infection (FIG. 3).

EXAMPLE 6

Factors Influencing Cytocapacity Test and CD34+ Cell Number

For age, gender, diagnosis and pretreatment with chemotherapy and radiotherapy, no significant correlation with the cytocapacity test or the CD34+ cell number in the PBSC autografts was found.

TABLE 1

Characteristics of The Patients And Specification of High-dose Chemotherapy And Peripheral Blood Stem Cell (PBSC) Autograft.

| Patients | | |
|---|---|---|
| No. | 87 | 100% |
| Age (years) | | |
| Median | 53 | |
| Range | 18-68 | |
| Gender | | |
| Female | 36 | 41% |
| Male | 51% | 59% |
| Disease | | |
| Hodgkin's Diseas | 8 | 9% |
| Non-Hodgkin's Lymphoma | 21 | 24% |
| Multiple Myeloma | 58 | 67% |
| Previous Chemotherapy (cycles) | | |
| Median | 7 | |
| Range | 0-25 | |
| Previous Radiotherapy | | |
| Yes | 32 | 37% |
| No | 55 | 63% |
| High-dose chemotherapy | | |
| No. | 122 | 100% |
| BEAM | 5 | 4% |
| BEAC | 8 | 7% |
| BUCY | 22 | 18% |
| MEL | 87 | 71% |
| PBSC Autograft | | |
| First | 78 | 64% |
| Second | 41 | 33% |
| Third | 2 | 2% |
| Fourth | 1 | 1% |

TABLE 2

Leukocyte Counts In The Blood Before And After The Single G-CSF Dose, The Duration Of Leukopenia <1000/μL And The Objectives Of The Investigation.
The recovery of the absolute neutrophil count (ANC) and the platelet (PLT) recovery, the absence of fever >38.0° C. and the duration of intravenous (i.v.) antimicrobial therapy were the objectives of the investigation.

| High-dose chemotherapy | All | BUCY/ MEL | BEAC/ BEAM |
|---|---|---|---|
| No. of procedures | 122 | 109 | 13 |
| Leukocyte Counts | | | |
| Day-1 (pre test) | | | |
| Minimum | 1100 | 1800 | 1100 |
| 50. percentile | 3800 | 4000 | 2300 |

TABLE 2-continued

Leukocyte Counts In The Blood Before And After The Single G-CSF Dose, The Duration Of Leukopenia <1000/μL And The Objectives Of The Investigation.
The recovery of the absolute neutrophil count (ANC) and the platelet (PLT) recovery, the absence of fever >38.0° C. and the duration of intravenous (i.v.) antimicrobial therapy were the objectives of the investigation.

| High-dose chemotherapy | All | BUCY/MEL | BEAC/BEAM |
|---|---|---|---|
| Maximum | 10700 | 10700 | 6300 |
| Day 0 (post-test) | | | |
| Minimum | 600 | 3300 | 600 |
| 25. percentile | 11300 | 12500 | 2000 |
| 50. percentile | 15600 | 16200 | 4100 |
| 75. percentile | 22800 | 23300 | 5300 |
| Maximum | 59300 | 59300 | 11600 |
| Day +5 (aplasia) | | | |
| Minimum | 0 | 0 | 0 |
| 50. percentile | 100 | 100 | 100 |
| Maximum | 1100 | 1100 | 400 |
| Leukopenia <1000/μL (days) | | | |
| Minimum | 3 | 3 | 6 |
| 50. percentile | 6 | 5 | 7 |
| Maximum | 11 | 11 | 10 |
| Days to ANC >500/μL | | | |
| Minimum | 8 | 8 | 8 |
| 25. percentile | 8 | 8 | 8 |
| 50. percentile | 9 | 9 | 8 |
| 75. percentile | 10 | 10 | 9 |
| Maximum | 12 | 12 | 11 |
| Days to PLT >20000/μL | | | |
| Minimum | 8 | 8 | 8 |
| 25. percentile | 10 | 10 | 10 |
| 50. percentile | 10 | 10 | 10 |
| 75. percentile | 11 | 11 | 12 |
| Maximum | 24 | 23+ | 24 |
| Fever >38.0° C. | | | |
| No fever | 45% | 45% | 46% |
| i.v. Antimicrobials (days) | | | |
| Minimum | 0 | 0 | 0 |
| 50. percentile | 4 | 4 | 4 |
| Maximum | 28 | 28 | 17 |

TABLE 3

Correlation of the cytocapacity test and the CD34+ cell number of the PBSC autograft with the objectives of the investigation.

| | CD34+ × 10$^6$/kg | | | | Cytocapacity test | | | |
|---|---|---|---|---|---|---|---|---|
| | ≦2.5 | >2.5-≦5.0 | >5.0 | P Value | ≦25. | >25.-≦50. | >50. percentile | P Value |
| No. of procedures | 30 | 40 | 52 | | 32 | 31 | 59 | |
| Days to ANC > 500/μL | | | | <0.0001 | | | | 0.001 |
| Minimum | 8 | 8 | 8 | | 8 | 8 | 8 | |
| 25. percentile | 10 | 9 | 8 | | 9 | 8 | 8 | |
| 50. percentile | 10 | 9 | 8 | | 10 | 9 | 9 | |
| 75. percentile | 10 | 10 | 9 | | 10 | 10 | 9 | |
| Maximum | 12 | 11 | 10 | | 12 | 12 | 11 | |
| Days to PLT > 20000/μL | | | | <0.0001 | | | | <0.0001 |
| Minimum | 9 | 9 | 8 | | 9 | 8 | 8 | |
| 25. percentile | 11 | 10 | 9 | | 10 | 10 | 9 | |
| 50. percentile | 12 | 11 | 10 | | 12 | 10 | 10 | |
| 75. percentile | 13 | 12 | 11 | | 15 | 11 | 11 | |
| Maximum | 17+ | 24 | 23+ | | 24 | 14+ | 14 | |
| Fever > 38.0° C. | | | | 0.7 | | | | 0.03 |
| No fever | 33% | 43% | 54% | | 28% | 48% | 53% | |
| i.v. Antimicrobials (days) | | | | 0.3 | | | | 0.03 |
| Minimum | 0 | 0 | 0 | | 0 | 0 | 0 | |
| 25. percentile | 0 | 0 | 0 | | 2 | 0 | 0 | |
| 50. percentile | 5 | 3 | 5 | | 6 | 5 | 2 | |
| 75. percentile | 9 | 6 | 7 | | 10 | 7 | 6 | |
| Maximum | 13 | 17 | 28 | | 17 | 28 | 17 | |

EXAMPLE 7

Factors that Correlate with Hematopoietic Recovery

The cytocapacity test according as described hereinabove involves the measurement of parameters of a mammal or of parameters derived from a sample derived from a mammal which correlate with the hematopoietic recovery where the mammal has been subjected to administration of a hematopoietic growth factor. The parameter is preferably white blood cell count, or leukocyte cell count. The absolute values of the parameter measured is, as described above, preferably evaluated on a relative scale which is defined by the median (set as 1.0) of the distribution within a treatment group, that is, within a group of mammals receiving a similar or identical treatment. The term "similar or identical treatment" preferably relates to the treatment regimen comprising the doses of radiation therapy and chemotherapy, and the times of administration and kinds of drugs used therein. The parameters are preferably measured in a sample derived from the mammal, such as a body fluid or a biopsy. The biopsy is preferably taken from a site that contains, in a healthy mammal, immunologically active cells. The cells are preferably T cells, B cells, Granulocytes, Platelets, Monocytes, NK cells, and the like cells. The cells may be derived from an early or late stage in cell development and/or differentiation. The body fluid is preferably blood or derived from blood. The mammal is preferably a human. The growth factor is preferably G-CSF or a growth factor of similar activity in stimulating the hematopoietic system. For instance, angiotensin and/or angiotensin-derived peptides (Rodgers et al., Cancer Chemother Pharmacol 49(5):403-11, 2002), interleukin-1 beta (Lebedev et al., Radiats Biol Radioecol 42(1):60-4, 2002), interleukin-8 (Terashima et al., Blood 92(3):1062-69, 1998; Laterveer et al., Blood 85(8):2269-75, 1995; Laterveer et al., Blood 87(2): 781-88, 1996) and interleukin-11 (Saitoh et al., Cytokine 13(5):287-94 2001), may exhibit such activity. The stimulating activity on the hematopoietic system may vary from one factor to the other. For instance, interleukin-11 preferably acts as on megakaryopoiesis. Also non-peptide factors, such as PGG-glucan, may act in stimulating hematopoiesis (Turnbull et al., Acta Haematol 102(2):66-71, 1999).

The factors that may be measured include cell count. This is preferably measured in a sample derived from the mammal, preferably a human, the sample being preferably a blood sample or blood-derived sample. The blood derived sample preferably contains white blood cells, also preferably leukocytes. The cells counted are preferably T cells, NK cells, Granulocytes, eosinophilic cells, Monocytes, Neutrophils, thrombocytes, lymphocytes, B cells, and the like cells. The cells counted preferably are of hematopoietic origin, more preferably cells that are derived from precursor and/or stem cells.

The parameter is also possibly derived from measurement of a marker, preferably a cell surface marker. Such markers include CD3, CD4, CD8, CD20, B7, CD45, CD34, CD36, CD56, CD19, CD20-24, CD25, CD 37, CD79 alpha and/or beta, CD 2, CD5, CD7, CD43, CD45 (leukocyte common antigen LAK) CD45R0, CD56, flow cytometry side scatter, flow cytometry forward scatter, S-100 markers which react with all lymphoid cells, CD30, CD45RA, CD74, CDw75, CDw76, CD79, kappa light chain, lambda light chain. Additional markers are those that are associated with cell proliferation, for instance, the Ki-67 marker. Further markers are associated with cell death, preferably apoptosis or necrosis. A number of markers or methods are known to the person skilled in the art for the detection of apoptosis. For instance, annexin V, DNA laddering, nucleus condensation, nucleus fragmentation, single strand DNA labeling, cytochrome c release and the cleavage of substrates (e.g. PARP) by caspases are markers associated with apoptosis. Preferably, annexin V-labeling or caspase3/7 activity test can be employed.

The determination and/or measurement of the above parameters is well within the knowledge of the person of skill in the art. For instance, assays for the surface and cell internal protein markers mentioned above are available commercially from Dako Cytomation Denmark A/S, Produktionsvej 42, 2600 Glostrup, Denmark, or a subsidiary thereof.

Any of the above markers may therefore be correlated, by carrying out the cytocapacity test as described in the above example 1, and using as an additional parameter the marker as described above. The additional parameter is then correlated with the hematopoietic recovery in a like manner as the leukocyte count, the correlation of which to hematopoietic recovery is described in example 1 hereinabove. A correlation better than that of leukocyte count with hematopoietic recovery, and/or with the therapy- and outcome-related factors as described in the examples herein, is preferred.

EXAMPLE 8

The Cytocapacity Test in a Group of Patients with Multiple Myeloma or Relapsed Lymphoma Patients and Methods Patients The investigation was performed in 86 patients with multiple myeloma (MM) or relapsed lymphoma (LYM). 49 patients (57%) were male, 37 patients (43%) were female. The median age was 53 years (range 18-68 years). Before high-dose therapy, the patients had received a median of 6 cycles of chemotherapy (range 0-25 cycles). Radiation therapy had been given to 29 patients (34%). The patients gave informed consent to their treatment. This patient cohort partially overlaps with the patient cohort of Examples 1-6.

Blood Stem Cell Mobilization, Harvesting, Processing and Cryopreservation

In the vast majority of patients, the IEV regimen with G-CSF was used for stem cell mobilization. The IEV regimen consists of ifosfamide 2500 mg/m$^2$ intravenously day 1-3, epirubicin 100 mg/m$^2$ intravenously day 1 and etoposide 150 mg/m$^2$ intravenously day 1-3 followed by G-CSF (filgrastim; Amgen, Thousand Oaks, Calif., USA) at a dose of 5 µg/kg subcutaneously daily from day 5 until the completion of blood stem cell harvesting. Apart from individual dose reductions, patients with MM and age >=60 years received IEV in a 75% dosage since 2000. PBSCs were harvested when the post-nadir, G-CSF stimulated leukocyte count rose up to 5000-10000/µL or above using a COBE Spectra (COBE, Heimstetten, Germany) or an AS104 (Fresenius, St. Wendel, Germany) cell separator and standard programs. In some cases, harvested blood stem cells from a single leukapheresis underwent immunomagnetic B cell purging (MaxSep, Baxter Immunotherapy, Unterschleissheim, Germany) immediately after the collection. The blood stem cells were mixed with an equal volume of a freezing solution which was prepared with 5% HSA and 100% DMSO (Cryoserv, Tera Pharmaceuticals, Midvale, Utah, USA) (4:1). The final DMSO concentration was 10%. After computerized controlled-rate freezing, the bags containing the blood stem cells were stored in the vapor phase of liquid nitrogen.

CD34+ Cell Enumeration in the Blood Stem Cell Autograft

The determination of CD34+ cells was carried out according to the guidelines of ISHAGE (Sutherland et al. 1996) using a FACScan (BD, Mountain View, Calif., USA) or an EPICS XL-MCL (Electronics, Miami, Fla., USA) flow cytometer equipped with an argon laser. Whole blood was incubated for 30 minutes at 4° C. in the dark with the PE conjugated monoclonal anti-CD34 antibody and the FITC conjugated monoclonal anti-CD45 antibody followed by a wash and red blood cell lysis (BD). Before 1998, 20000 cells were analysed, 75000 cells thereafter. To exclude cell debris, platelets, remaining red cells and all CD45 negative cells, a forward scatter versus CD45 fluorescence dot plot was used. The double-positive CD34+/CD45+ cell population was then defined and backgated for low CD45 expression and low side scatter properties. The percentage of the so defined CD34+ cells was multiplied with the total nucleated cell content of the apheresis product to result in the absolute number of CD34+ cells harvested. The nucleated cell content was determined by automated cell counting using a Coulter STKS (Coulter, Miami, Fla., USA). The anti-CD34 antibody (HPCA-2), the anti-CD45 antibody (2D1) and the isotype controls used were from BD.

High-dose Therapy and Blood Stem Cell Transplantation

One hundred and twenty-eight high-dose chemotherapy courses in the 86 patients were investigated. Melphalan 200 mg/m$^2$ (MEL200) (Barlogie et al. 1997) was applied in 88 procedures (69%), melphalan 100 mg/m$^2$ (MEL100) (Palumbo et al. 1999) in 18 procedures (14%) and BUCY in 22 procedures (17%) (Schiller et al. 1994; Weaver et al. 1999). Autologous blood stem cell transplantation was performed 48 hours after the last dose of chemotherapy.

Application of G-CSF and Blood Cell Counts

The recombinant human G-CSF given subcutaneously after high-dose chemotherapy was filgrastim (Amgen, Thousand Oaks, Calif., USA) in 121 cases and lenograstim (Chugai, Japan) in 7 cases. The single G-CSF injection evaluated was given on the evening before autologous blood stem cell transplantation at a dose of 5 µg/kg, approximately 30 hours after the last chemotherapy infusion. The induced WBC peaks were measured with the routine blood tests on the next morning, 12-14 hours after the single G-CSF dose. The autologous blood stem cell transplantation was carried out approximately 2 hours after the routine blood test. From the day after transplantation, G-CSF was given daily at a dose of 5 µg/kg until post-nadir WBC counts were between 5000/µL and 10000/µL. Routine blood cell counts including a differential were performed on a Coulter STKS (Coulter, Miami, Fla., USA) daily from the start of high-dose therapy until the patients left the hospital.

Supportive Care

All the patients were hospitalized during high-dose therapy, autograft and the post-transplant phase and received the same supportive care. The antimicrobial prophylaxis consisted of the following: From the time of autograft until neutrophil recovery ciprofloxacin 2×250 mg daily was given. Oral amphotericin B suspension 4×1 mL was given during the entire hospital stay or alternatively, in case of oral amphotericin intolerance, oral fluconazole 1×100 mg daily. *Pneumocystis carinii* pneumonitis prophylaxis was given during the administration of high-dose chemotherapy with trimethoprim/sulfamethoxazole 160 mg/800 mg 2×1 daily, was stopped before transplantation and was continued after neutrophil recovery with 2×1 on two consecutive days per week for 6 months. In case of trimethoprim/sulfamethoxazole intolerance, alternatively a pentamidine inhalation with 300 mg was performed every 4 weeks for 6 months from autograft. Intravenous acyclovir was given at a dose of 2×500 mg from the start of high-dose therapy until neutrophil recovery. Red blood cell products and single-donor platelets were substituted to maintain a hemoglobin level above 80 g/L and a platelet-count above 10000/µL. All blood cell products were CMV negative, were irradiated with 30 Gy and were transfused through a leukocyte reduction filter. Empirical intravenous antimicrobial therapy was started during neutropenia after a single oral temperature >38.5° C. or when fever >38.0° C. was present over at least one hour and was carried out according to previously published guidelines (Hughes et al. 1997). The initial treatment was carried out with piperacillin/tazobactam plus gentamicin. Escalation was performed with meropenem/vancomycin. If fever persisted on days 5-7, intravenous amphotericin B was added. The antimicrobial treatment was continued until neutrophil recovery and at least 24 hours after the resolution of fever. Patients were discharged from the hospital after neutrophil and platelet recovery and after the cessation of antimicrobial treatment.

Assessment of Hematopoietic Recovery and Infection

Neutrophil recovery was defined as the first day with a neutrophil count above 500/µL from the day of autograft. Platelet recovery was defined as the first day with an unsubstituted platelet count above 20000/µL from the day of autograft. The observation period was from high-dose therapy until the patients left the hospital. The assessment of infection was carried out according to previously published criteria (Link et al. 1994).

Objectives and Statistical Analysis

The objectives of this investigation were to correlate the induced WBC peak as the indicator of the G-CSF reaction with the neutrophil and platelet recovery and the rate and type of infection and to compare these correlations with those obtained for the CD34+ cell number in the autologous blood stem cell autograft. All analyses presented (except for the demographic and disease baseline characteristics) are based on transplantation courses as units of observation.

The rates of neutrophil and platelet recovery over time were estimated using the product-limit method according to Kaplan and Meier (Kaplan and Meier, 1958) and prognostic subgroups were compared by use of the log-rank test (Peto and Peto, 1972). Differences in continuous variables between prognostic groups were tested by Wilcoxon-Mann-Whitney or Kruskal-Wallis analysis, depending on the number of groups. In case of nominal or ordered categories, Fisher's exact or chi$^2$ tests for trend were applied. In order to examine the independent impact of the predictive factors with regard to the different end-points, multivariate analyses were carried out with stratified versions of the respective tests, Cox (Cox, 1972) or logistic regression models depending on the nature of the outcome variable. All reported p-values result from two-sided tests.

The Host G-CSF Reaction

A single subcutaneous G-CSF injection (5 µg/kg) was administered early after 128 high-dose chemotherapy courses in 86 patients with multiple myeloma or lymphoma. At this time point, the median WBC count was 4100/µL (range 1800-10700/µL) and the median platelet count was 197000/µL (range 24000-640000/µL). The G-CSF induced WBC peak was measured 12-14 hours later. These transient WBC peaks had a different magnitude (FIG. 4) and consisted of around 90% neutrophils. The median WBC peak was 17400/µL (range 3300-60600/µL). The distribution of WBC peaks is shown in FIG. 5A. Colony-forming cells or CD34+ cells were not detected within these WBC peaks. After the WBC peak, the WBC counts declined and severe leukopenia (<200/μL) followed in all cases.

Prediction of the Hematopoietic Recovery

Autologous blood stem cell transplantation was performed after the measurement of the G-CSF reaction with a median of $3.92 \times 10^6$ CD34+ cells/kg (range 0.9-21.2). The time to neutrophil engraftment (>500/μL) was a median of 9 days (range 8-12) and the time to platelet engraftment (>20000/μL) was a median of 10 days (range 8-25).

The G-CSF reaction predicted the neutrophil (p<0.0001) and the platelet engraftment (p<0.0001) (table 4). The number of transplanted CD34+ cells also predicted the neutrophil (p<0.0001) and platelet engraftment (p<0.0001), as expected. Other patient or treatment characteristics and the WBC count before G-CSF did not correlate with the hematopoietic recovery (table 4). The correlation between the G-CSF reaction and the CD34+ cell number was weak (r=0.21; p=0.02). In multivariate analysis in a Cox model, the prediction of the hematopoietic recovery by the G-CSF reaction was independent from the effect of transplanted CD34+ cells (table 5).

Prediction of Infection

Fever >38.0° C. was present in 69 of 128 procedures (54%). Infections were documented in 29 procedures (23%). The G-CSF reaction highly significantly predicted the rate of documented infections (p<0.0001). Leukopenia <1000/μL lasted for a median of 5 days (range 3-11). As could be expected, also the duration of leukopenia correlated with the rate of documented infections (p=0.003). In multivariate analysis performed as a logistic regression, the G-CSF reaction was independent from leukopenia duration in the prediction of infection and emerged as the dominant prognostic factor (p<0.0001) (table 5). There was no correlation between the rate of documented infection and the number of transplanted CD34+ cells or other patient and treatment characteristics (table 4). A number of factors correlated with the occurrence of fever, but none of these retained independent significance in multivariate analysis.

The vast majority of documented infections (86%) occurred at a low G-CSF reaction (FIG. 5 and table 6). Bacterial isolates from the blood stream were predominantely coagulase-negative staphylococci. Also, the majority of pneumonias (83%) and all the invasive fungal infections and treatment-related deaths were associated with a low G-CSF reaction.

In 39 patients where a first and second high-dose chemotherapy course was analysed, the G-CSF reaction decreased from a median of 21700/μL WBC's (range 6400-59300/μL) after the first to a median of 15600/μL WBC's (range 3300-24800/μL) after the second high-dose chemotherapy. At the same time, the proportion of documented infection increased by 38%.

TABLE 4

Univariate analysis of the association of factors with stem cell engraftment and risk of infection.

|  | Engraftment | | Infection |
| --- | --- | --- | --- |
|  | ANC >500/μL | PLT >22.000/μL | Documented |
| Age (≦53 vs. >53 years) | 0.19 | 0.40 | 0.53 |
| Gender (male vs. female) | 0.96 | 0.53 | 0.68 |
| Diagnosis (MM vs. LYM) | 0.96 | 0.83 | 0.76 |
| Previous Chemotherapy (≦6 vs. >6 cycles) | 0.14 | 0.81 | 0.40 |
| Previous Radiation (Yes vs. No) | 0.52 | 1.00 | 0.65 |
| CD34 + cells transplanted (<2.5 vs. 2.5-5.0 vs. >5.0) | <0.0001 | <0.0001 | 0.79 |
| G-CSF reaction (1. vs. 2. vs. 3./4. quartile) | <0.0001 | <0.0001 | <0.0001 |
| WBC count before G-CSF (<4000/μL vs. ≧4000/μL) | 0.06 | 0.54 | 0.20 |
| Days with leukocytes <1000/μL (≦5 days vs. >5 days) | — | — | 0.003 |
|  | p-value | | |

ANC = Absolute Neutrophil Count;
PLT = Platelet Count;
MM = multiple myeloma;
LYM = lymphoma.

TABLE 5

Multivariate analysis of relevant factors for stem cell engraftment and documented infections.

|  | Engraftment | |
| --- | --- | --- |
|  | ANC >500/μl | PLT >20.000/μl |
| CD34 +cells transplanted | <0.0001 | <0.0001 |
| G-CSF reaction | 0.02 | 0.0006 |
|  | p-value | |

|  | Documented infections |
| --- | --- |
| G-CSF reaction | <0.0001 |
| Days with leukocytes <1.000/μL | >0.2 |
|  | p-value |

TABLE 6

Correlation between G-CSF reaction and type of documented infection.

| G-CSF reaction N | Quartile 1 32% | Quartile 2 32% | Quartile 3 32% | Quartile 4 32% |
|---|---|---|---|---|
| Blood stream infection | 22 | 12 | 3 | 0 |
| Coag.-neg. Staphyl. | 19 | 9 | 3 | |
| Streptococcus | 3 | | | |
| Propionibacterium | | 3 | | |
| Pneumonia | 25 | 6 | 6 | 0 |
| Invasive fungal infection | 6 | 0 | 0 | 0 |
| Severe enterocolitis | 3 | 6 | 0 | 0 |
| Other infections | 12 | 6 | 6 | 0 |
| Sinusitis | | 3 | 3 | |
| Cholecystitis | 3 | | | |
| Soft-tissue infection | 6 | | | |
| Myelitis | 3 | | | |
| Catheter entry-site infection | | | 3 | |
| Port-sepsis | | 3 | | |
| Overall incidence | 47 | 31 | 12 | 0 |
| Treatment-related mortality | 6 | 0 | 0 | 0 |

In this investigation we found that the reaction of the host to a single dose of pharmacological G-CSF before a phase of myelosuppression follows can be a predictor of critical hematopoietic functions during the course and for overcoming myelosuppression. This highlights the potential of G-CSF and suggests that G-CSF could be used in a diagnostic procedure. To assess and predict the capacity of host defense mechanisms to fight infection and to compensate cytopenia before a manifestation of myelosuppression has not been possible so far. The G-CSF reaction provokes a leukocyte mobilization by targeting the bone marrow microenvironment and directly represents an effector cell response. This is conceptually different from measuring cytokine levels. Our investigation suggests a microenvironmental capacity of host defense which apparently can be targeted and tested by pharmacological G-CSF in vivo.

The number of transplanted CD34$^+$ cells is the major relevant factor for stem cell engraftment after high-dose chemotherapy (Bensinger et al. 1995; Tricot et al. 1995; Weaver et al. 1995; Ketterer et al. 1988). This was confirmed in our study. The G-CSF reaction, however, predicted stem cell engraftment independently from the number of transplanted CD34$^+$ cells. The G-CSF reaction therefore represents an important independent factor for the hematopoietic recovery which is maintained during reformation of a functional hematopoietic microenvironment following autologous stem cell transplantation.

The duration of leukopenia is a major known factor for the risk of infection in the myelosuppressed host (Bodey et al. 1966). This could be recapitulated in our study. The G-CSF reaction, however, was independent from leukopenia duration in the prediction of infection and emerged as the dominant prognostic factor ($p<0.0001$). G-CSF is the central mediator in the host response to neutropenia and infection (Watari et al. 1989; Kawakami et al. 1990). The host leukocyte response provoked by pharmacological G-CSF possibly was a premature reflection of the potential of this G-CSF-inducible "emergency reaction" during myelosuppression. For the transplanted CD34$^+$ cell number, no correlation with the rate of documented infections was found ($p=0.79$). As long as a regular neutrophil engraftment occurs, there seems to be no further impact of CD34$^+$ cell number on the rate of infection. Experiments in mice reveal the influence of G-CSF on microenvironmental functionality. In transgenic mice constitutively expressing high levels of human G-CSF, megakaryocytopoiesis in the bone marrow was augmented although G-CSF has not been assigned a specific role in megakaryocytopoiesis (Fujita et al. 2001). In transplantation experiments, it was shown that this augmentation of megakaryocytopoiesis was dependent on microenvironmental changes induced by transgenic human G-CSF. This qualitatively altered microenvironment allowed a faster platelet recovery following hematopoietic transplantation. This fits to our clinical finding that the G-CSF reaction is an independent predictor of platelet recovery. In G-CSF knock-out mice, which did not express G-CSF, a chronic neutropenia, a diminution of progenitor cells, a reduced fast mobilizability of leukocytes by a single pharmacological dose of G-CSF and a higher susceptibility to experimental infection was found (Lieschke et al. 1994). These findings in part correspond to our observations in patients with a low G-CSF reaction. One could speculate that developmental effects of G-CSF on the microenvironment are reflected in the G-CSF reaction.

The high-dose chemotherapy setting likely favored the identification of the predictive potential of the G-CSF reaction because of the high degree of myelosuppression, the associated higher number of infectious episodes and the close monitoring of patients in the hospital. In contrast to the passive observation of a neutrophil nadir during myelosuppression after chemotherapy to draw conclusions about neutropenic events in the further course of therapy (Silber et al. 1998), the G-CSF reaction can be assessed at normal WBC counts and obviously is dependent on the presence of mobilizable leukocytes in the bone marrow. The in part very high leukocyte peaks and their high variability in our investigation suggest a maximum mobilizing effect which allows to recognize differences between patients. The high-dose chemotherapy given immediately before probably exerted a priming effect for the mobilization with G-CSF, since the observed strong mobilizing effects usually are not observed at a G-CSF dose of 5 µg/kg. The effects of pharmacological G-CSF are dose-dependent. A strong mobilizing effect during steady-state hematopoiesis or after conventional chemotherapy is observed only at G-CSF doses of 10 µg/kg or above (Morstyn et al. 1988; Morstyn et al. 1989).

About one third of autologous blood stem cell transplants worldwide are performed in multiple myeloma. The vast majority of these patients receives melphalan or busulfan/cyclophosphamide high-dose chemotherapy before transplantation, as it was applied in our investigation. In these patients, the G-CSF reaction could provide a basis to administer risk-stratified supportive care in controlled clinical trials (Meisenberg et al. 1997; Herrmann et al. 1999; Kern et al. 1999; Freifeld et al. 1999). Moreover, the G-CSF reaction could play a role in other areas like chemotherapy without stem cell transplantation for solid tumors. It would be interesting to investigate whether the actual need for pharmacological G-CSF could be determined on the basis of the G-CSF reaction. The G-CSF reaction also could contribute to the development of novel prophylactic strategies against infection (Noursadeghi et al. 2002).

EXAMPLE 9

The Cytocapacity Test Predicts the Duration of Leukopenia and Neutropenia

The following analysis was done on the cases of example 8. The cytocapacity test (WBC peak) predicts the duration of leukopenia and neutropenia (table 7).

TABLE 7

Correlation of the duration of leukopenia and neutropenia with the cytocapacity test (WBC peak) and the number of transplanted CD34+ cells.

| Quartile | WBC peak | | | | CD34+ cells × 10⁶/kg | | |
|---|---|---|---|---|---|---|---|
| | 1 | 2 | 3 | 4 | <2.5 | 2.5-5.0 | >5.0 |
| Leukopenia < 1.000/μL (Days) | | | p < 0.001 | | | | p < 0.001 |
| Minimum | 4 | 4 | 3 | 3 | 5 | 4 | 3 |
| 25. Percentile | 6 | 5 | 5 | 5 | 6 | 5 | 4 |
| 50. Percentile | 6 | 6 | 5 | 5 | 6 | 6 | 5 |
| 75. Percentile | 7 | 6 | 6 | 5 | 7 | 6 | 5 |
| Maximum | 11 | 9 | 7 | 8 | 11 | 8 | 8 |
| Neutropenia < 500/μL (Days) | | | p < 0.001 | | | | p < 0.001 |
| Minimum | 4 | 4 | 3 | 3 | 4 | 3 | 3 |
| 25. Percentile | 5 | 5 | 4 | 4 | 6 | 5 | 4 |
| 50. Percentile | 6 | 5 | 5 | 5 | 6 | 5 | 5 |
| 75. Percentile | 7 | 6 | 6 | 5 | 7 | 6 | 5 |
| Maximum | 9 | 9 | 7 | 7 | 9 | 8 | 7 |

EXAMPLE 10

The Leukocyte or White Blood Cell (WBC) Peak as the Result of the Cytocapacity Test is Very Similar to the Respective Neutrophil Peak The following data (table 8) is based on the cases of example 8.

TABLE 8

Correlation between the induced WBC and the neutrophil peak.

| | WBC Peak (/μL) | Neutrophil Peak (/μL) |
|---|---|---|
| Minimum | 3.300 | 3.100 |
| 25. Percentile | 12.800 | 12.100 |
| 50. Percentile | 17.400 | 16.700 |
| 75. Percentile | 23.300 | 22.400 |
| Maximum | 60.600 | 56.300 |
| | | r = 0.998 |

EXAMPLE 11 the Cytocapacity Test after Myelosuppressive Chemotherapy without Hematopoietic Stem Cell Transplantation forty-eight patients with lymphoma or multiple myeloma received the iev chemotherapy followed by G-CSF for tumor reduction and stem cell mobilization as specified in Example 8. The first G-CSF injection was given on day 5 of the regime and the induced leukocyte peak on day 6 was taken as the cytocapacity test. The leukocyte count rose from a median of 5.000/μL (range 1.500-8.200/μL) to a median of 10.100/μl (range 300-46.700/μL). The graduation of the leukocyte peak predicted the risk of fever and infection (p<0.05) (table 9) during the following phase of myelosuppression. A hematopoietic transplantation was not carried out.

TABLE 9

Correlation of the cytocapacity test with fever and infection after myelosuppressive chemotherapy with the IEV regime.

| Leukocyte peak (=cytocapacity test) | N | Fever and infection | |
|---|---|---|---|
| <=median | 23 | 7 | (30%) |
| | | | p<0.05 |
| >median | 23 | 1 | (4%) |

REFERENCES

Arseniev, Blood 1997; 89: 1116-1118
Asano, The American Journal of Pediatric Hematology/Oncology 1991; 13: 400-413
Attal, N Engl J Med 1996; 335: 91-97.
Barlogie, Blood 1997; 89: 789-793.
Bensinger, J Clin Oncol 1995; 13: 2547-2555.
Beyer, J Clin Oncol 1995; 13:1328-1335.
Blay, J Clin Oncol 1996; 14: 636-643.
Bodey, Ann Intern Med 1966; 64: 328-340.
Bolwell, Bone Marrow Transplant 1997; 20: 459-463.
Bronchud, Br J Cancer 1988; 58: 64-69.
Chatta, Blood 1994; 84: 2923-2929.
Cox, J. Roy Stat Soc 1972; (B) 34: 187-202.
Dührsen, Blood 1988; 72: 2074-2081.
Fujita, Exp Hematol 2001; 29: 1010-1018.
Gabrilove, J Clin Invest 1988; 82: 1454-1461.
Freifeld, N Engl J Med 1999; 341: 305-311.
Herrmann, Bone Marrow Transplant 1999, 24: 1213-1217.
Hughes, Clin Infect Dis 1997; 25: 551-573.
Kaplan, J Am Stat Ass 1958; 53: 457481.
Kawakami Blood 1990; 76:1962-1964.
Kern, N Engl J Med 1999; 341: 312-318.
Ketterer, Blood 1998; 91: 3148-3155.
Klastersky, J Clin Oncol 2000; 18: 3038-3051.
Kolbe, Bone Marrow Transplant 1997; 19: 143-147.
Kubota, J. Biochem. 1990; 107: 486-492.
Laterveer et al., Blood 85(8):2269-75, 1995.
Laterveer et al., Blood 87(2):781-88, 1996.
Lenhoff, Blood 2000; 95: 7-11.

Lieschke, Blood 1994; 84:1737-1746.
Linch, Lancet 1993; 341: 1051-1054.
Link, Ann. Hematol. 1994; 69: 231-243
Lord, Proc. Natl. Acad. Sci. USA 1989; 86: 9499-9503.
Meisenberg, J Clin Oncol 1997; 15: 11-17.
Molineux, Blood (1990); 76: 2153-2158.
Morstyn, Lancet 1988; 1: 667-672.
Morstyn, J Clin Oncol 1989; 7:1554-1562.
Noursadeghi, J Immunol 2002; 169: 913-919.
Ozer, J Clin Oncol 2000; 18:3558-3585.
Palumbo, Blood 1999; 94:1248-1253.
Peto,. J R Stat Soc A 1972; 135:185-206.
Pettengell, Blood 1993; 82: 3770-3777.
Philip, N Engl J Med 1995; 333: 1540-1545.
Pizzo, N Engl J Med 1993; 328: 1323-1332.
Reich, Bone Marrow Transplant 2001; 27: 525-529.
Rubenstein, Cancer 1993; 71: 3640-3646.
Schiller, Bone Marrow Transplant 1994; 14:131-136.
Schmitz, Lancet 1996; 347: 353-357.
Silber, J Clin Oncol 1998; 16: 2392-2400.
Sutherland, J Hematotherapy 1996; 5: 213-226.
Talcott, J Clin Oncol 1992; 10: 316-322.
Talcott, J Clin Oncol 1994; 12: 107-114.
Terashima et al., Blood 92(3):1062-69, 1998
Tricot, Blood 1995; 85: 588-596.
Watari, Blood 1989; 73:117-122.
Weaver, Bone Marrow Transplant 1998; 21: 383-389
Weaver, Blood 1995; 86: 3961-3969.
Welte, Blood 1996; 88:1907-1929

The invention claimed is:

1. A method for predicting the risk of diseases, disorders or complications associated with cytotoxic therapy and/or hematopoietic cell transplantation in a subject comprising the step of:
  (a) identifying a subject with multiple myeloma or lymphoma that has received cytotoxic therapy comprising chemotherapy;
  (b) administering to the subject a single dose of G-CSF sufficient to allow mobilization or release of the leukocytes from hematopoietic production and storage tissue and sites of migration into the blood of the subject; and
  (c) determining whether the subject has high, medium or low hematopoietic cytocapacity; wherein a subject with a high hematopoietic cytocapacity indicates a reduced risk of disease, disorder, or complications associated with cytotoxic therapy and/or hematopoietic cell transplantation relative to a subject with low or medium hematopoietic cytocapacity, wherein the disease, disorder, or complications are selected from fever greater than 38° C., severity and duration of neutropenia, duration of leucopenia, infection, duration of i.v. antibiotic treatment, time for platelet recovery, or time for neutrophil recovery.

2. A method for selecting a suitable antimicrobial prophylaxis or therapy for a subject, wherein said method comprises the steps of the method of claim 1 and the further step (d) of selecting a suitable antimicrobial prophylaxis or therapy for said subject based on the result obtained in step (c).

3. A method according to claim 2, wherein said prophylaxis or therapy is a prophylaxis or therapy for the treatment, prevention or amelioration of an infection.

4. A method according to claim 3, wherein said infection is selected from the group of fungal, viral, protozoal, parasitical and bacterial infections.

5. A method according to claim 3, wherein said infection is selected from the group consisting of pneumonia, invasive fungal infection, enterocolitis, soft-tissue infection, and sepsis.

6. A method for selecting a suitable prophylaxis or therapy for neutropenic fever for a subject, wherein said method comprises the steps of the method of claim 1 and the further step (d) selecting a suitable prophylaxis or therapy for neutropenic fever for said subject based on the result obtained in step (c).

7. A method for selecting a suitable amount of hematopoietic stem cells to be transfused for the therapy of a subject, wherein said method comprises the steps of the method of claim 1 and the further step (d) of selecting the amount of said cells to be transfused for the therapy of a subject based on the result obtained in step (c).

8. A method for selecting a suitable amount of a hematopoietic growth factor or cytokine for the treatment of a subject, wherein said method comprises the steps of the method of claim 1 and the further step(d) selecting a suitable amount of a hematopoietic growth factor or cytokine for the treatment of said subject based on the result obtained in step (c).

9. The method of claim 1, wherein said subject is a human.

10. The method of claim 1, wherein said cytotoxic therapy comprises high-dose chemotherapy.

11. The method or composition of claim 10, wherein said high-dose chemotherapy comprises administration of melphalan, busulfan, cyclophosphamide, carmustine, etoposide, or cytarabine.

12. The method of claim 1, wherein said cytotoxic therapy comprises myelosupressive chemotherapy.

13. The method or composition of claim 12, wherein said myelosupressive chemotherapy comprises the administration of cyclophosphamide, etoposide, carmustine, cytarabine, melphalan, busulfan, doxorubicin, epirubicin, paclitaxel, docetaxel, thiotepa, fludarabine, vincristine, bendamustine, cisplatin, carboplatin, daunorubicin, fluorouracil, gemcitabine, idarubicin, ifosfamide, irinotecan, methotrexate, mitoxantrone, oxaliplatin, treosulfan, vinblastine, or vinorelbine.

14. The method of claim 1, wherein said cytotoxic therapy comprises radiotherapy, or wherein said subject suffers from a primary or secondary bone marrow disease, an autoimmune disease, a hereditary disease or disorder or an infection.

15. The method of claim 1, wherein said G-CSF is filgrastim or lenograstim.

16. The method of claim 1, wherein said dose of G-CSF is selected from a range of 1 to 20 g/kg body weight of the subject.

17. The method of claim 1, wherein said dose of G-CSF is 1.0, 2.5, 5, 7.5, or 10 g/kg body weight of the subject.

18. The method of claim 1, wherein said time sufficient to allow mobilization or release of the leukocytes is in the range of 1 to 120 hours.

19. The method of claim 1, wherein said time sufficient to allow mobilization or release of the leukocytes is at least 1 hour, at least 2 hours, at least 6 hours, at least 10 hours, at least 12 hours, at least 14 hours or at least 18 hours.

20. The method of claim 1, wherein the complications are selected from fever greater than 38° C. or severity and duration of neutropenia.

21. The method of claim 1, wherein the complication is fever greater than 38° C.

22. The method of claim 1, wherein the complication is duration of neutropenia.

23. The method of claim 1, wherein the complication is infection.

24. The method of claim 2, wherein the fever is neutropenic fever.

* * * * *

UNITED STATES PATENT AND TRADEMARK OFFICE
CERTIFICATE OF CORRECTION

| | |
|---|---|
| PATENT NO. | : 7,815,921 B2 |
| APPLICATION NO. | : 10/508509 |
| DATED | : October 19, 2010 |
| INVENTOR(S) | : Christian Straka |

It is certified that error appears in the above-identified patent and that said Letters Patent is hereby corrected as shown below:

Claim 14, column 39, line 20, before the word "suffers" insert -- further --.

Claim 16, column 40, line 2, "1 to 20 g/kb" should read -- 1 to 20 µg/kg --.

Claim 17, column 40, line 5, "10 g/kg" should read -- 10µg/kg --.

Claim 22, column 40, line 19, before the word "duration" insert -- severity and --.

Signed and Sealed this
Fourth Day of January, 2011

David J. Kappos
*Director of the United States Patent and Trademark Office*

SEQUENCE LISTING

```
<160> NUMBER OF SEQ ID NOS: 4

<210> SEQ ID NO 1
<211> LENGTH: 207
<212> TYPE: PRT
<213> ORGANISM: Homo sapiens

<400> SEQUENCE: 1

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Val Ser Glu Cys Ala Thr Tyr Lys Leu Cys His Pro Glu Glu Leu
65                  70                  75                  80

Val Leu Leu Gly His Ser Leu Gly Ile Pro Trp Ala Pro Leu Ser Ser
                85                  90                  95

Cys Pro Ser Gln Ala Leu Gln Leu Ala Gly Cys Leu Ser Gln Leu His
            100                 105                 110

Ser Gly Leu Phe Leu Tyr Gln Gly Leu Leu Gln Ala Leu Glu Gly Ile
        115                 120                 125

Ser Pro Glu Leu Gly Pro Thr Leu Asp Thr Leu Gln Leu Asp Val Ala
    130                 135                 140

Asp Phe Ala Thr Thr Ile Trp Gln Gln Met Glu Glu Leu Gly Met Ala
145                 150                 155                 160

Pro Ala Leu Gln Pro Thr Gln Gly Ala Met Pro Ala Phe Ala Ser Ala
                165                 170                 175

Phe Gln Arg Arg Ala Gly Gly Val Leu Val Ala Ser His Leu Gln Ser
            180                 185                 190

Phe Leu Glu Val Ser Tyr Arg Val Leu Arg His Leu Ala Gln Pro
        195                 200                 205

<210> SEQ ID NO 2
<211> LENGTH: 204
<212> TYPE: PRT
<213> ORGANISM: Homo sapiens

<400> SEQUENCE: 2
```

```
Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
                100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
                180                 185                 190

Val Ser Tyr Arg Val Leu Arg His Leu Ala Gln Pro
                195                 200

<210> SEQ ID NO 3
<211> LENGTH: 174
<212> TYPE: PRT
<213> ORGANISM: Homo sapiens

<400> SEQUENCE: 3

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
                100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

```
<210> SEQ ID NO 4
<211> LENGTH: 174
<212> TYPE: PRT
<213> ORGANISM: Homo sapiens

<400> SEQUENCE: 4

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```